(12) United States Patent
Nishioka

(10) Patent No.: US 11,304,669 B2
(45) Date of Patent: Apr. 19, 2022

(54) X-RAY DIAGNOSIS APPARATUS, MEDICAL IMAGE PROCESSING APPARATUS, MEDICAL IMAGE PROCESSING SYSTEM, AND MEDICAL IMAGE PROCESSING METHOD

(71) Applicant: CANON MEDICAL SYSTEMS CORPORATION, Otawara (JP)

(72) Inventor: Takahiko Nishioka, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 409 days.

(21) Appl. No.: 16/157,556

(22) Filed: Oct. 11, 2018

(65) Prior Publication Data
US 2019/0110767 A1    Apr. 18, 2019

(30) Foreign Application Priority Data

Oct. 12, 2017  (JP) .............................. JP2017-198741
Aug. 14, 2018  (JP) .............................. JP2018-152591

(51) Int. Cl.
*A61B 6/12*    (2006.01)
*A61B 6/00*    (2006.01)
(Continued)

(52) U.S. Cl.
CPC ................ *A61B 6/12* (2013.01); *A61B 6/032* (2013.01); *A61B 6/4035* (2013.01);
(Continued)

(58) Field of Classification Search
CPC .. A61B 6/03; A61B 6/032; A61B 6/46; A61B 6/461; A61B 6/466; A61B 6/467; A61B 6/469; A61B 6/481; A61B 6/504; A61B 6/52; A61B 6/5217; A61B 34/20; A61B 5/06; A61B 5/1128; A61B 2090/376; A61B 2090/3762; A61B 2090/3764;
(Continued)

(56) References Cited

U.S. PATENT DOCUMENTS

| 8,644,913 | B2 * | 2/2014 | Simpson | ................... A61B 6/12 |
| | | | | 600/478 |
| 10,779,786 | B2 * | 9/2020 | Sakaguchi | ............. A61B 6/504 |

(Continued)

FOREIGN PATENT DOCUMENTS

| JP | 2009-72317 | 4/2009 | |
| WO | WO-2014058838 A1 * | 4/2014 | ............... G06T 7/75 |
| WO | WO-2014124447 A1 * | 8/2014 | ........... A61B 6/5264 |

*Primary Examiner* — Peter Luong
(74) *Attorney, Agent, or Firm* — Oblon, McClelland, Maier & Neustadt, L.L.P.

(57) ABSTRACT

An X-ray diagnosis apparatus according to an embodiment includes processing circuitry. The processing circuitry is configured to extract a characteristic site in a lumen that may be a constraint during insertion of a surgical device, from medical image data used for determining a path through which the surgical device is to be inserted. On the basis of the characteristic site, the processing circuitry is configured to determine a tip end direction defined in accordance with a curved shape of a tip end part of the surgical device, in each of a plurality of positions on the path. The processing circuitry is configured to output path information including the tip end direction in each of the positions on the path.

20 Claims, 10 Drawing Sheets

(51) Int. Cl.
  *A61M 25/09* (2006.01)
  *A61M 25/01* (2006.01)
  *A61B 6/03* (2006.01)

(52) U.S. Cl.
  CPC ............ *A61B 6/4441* (2013.01); *A61B 6/463* (2013.01); *A61B 6/487* (2013.01); *A61B 6/488* (2013.01); *A61B 6/503* (2013.01); *A61B 6/504* (2013.01); *A61B 6/5223* (2013.01); *A61B 6/5235* (2013.01); *A61B 6/5288* (2013.01); *A61M 25/0108* (2013.01); *A61M 25/09* (2013.01)

(58) Field of Classification Search
  CPC ......... G06T 7/0012; G06T 7/70; G06T 11/00; G06T 11/001; G06T 15/00; G06T 2207/10072; G06T 2207/10081; G06T 2207/10116; G06T 2207/30101; G06T 2207/30104; G06T 2211/00; G06T 2211/40; G06T 2211/404
  See application file for complete search history.

(56) References Cited

U.S. PATENT DOCUMENTS

| | | | |
|---|---|---|---|
| 2009/0093712 A1* | 4/2009 | Busch | A61B 6/032 600/424 |
| 2011/0306867 A1* | 12/2011 | Gopinathan | A61B 5/064 600/407 |
| 2014/0111541 A1* | 4/2014 | Tolkowsky | A61M 25/09 345/632 |
| 2014/0236000 A1* | 8/2014 | Kozu | A61B 90/37 600/424 |

* cited by examiner

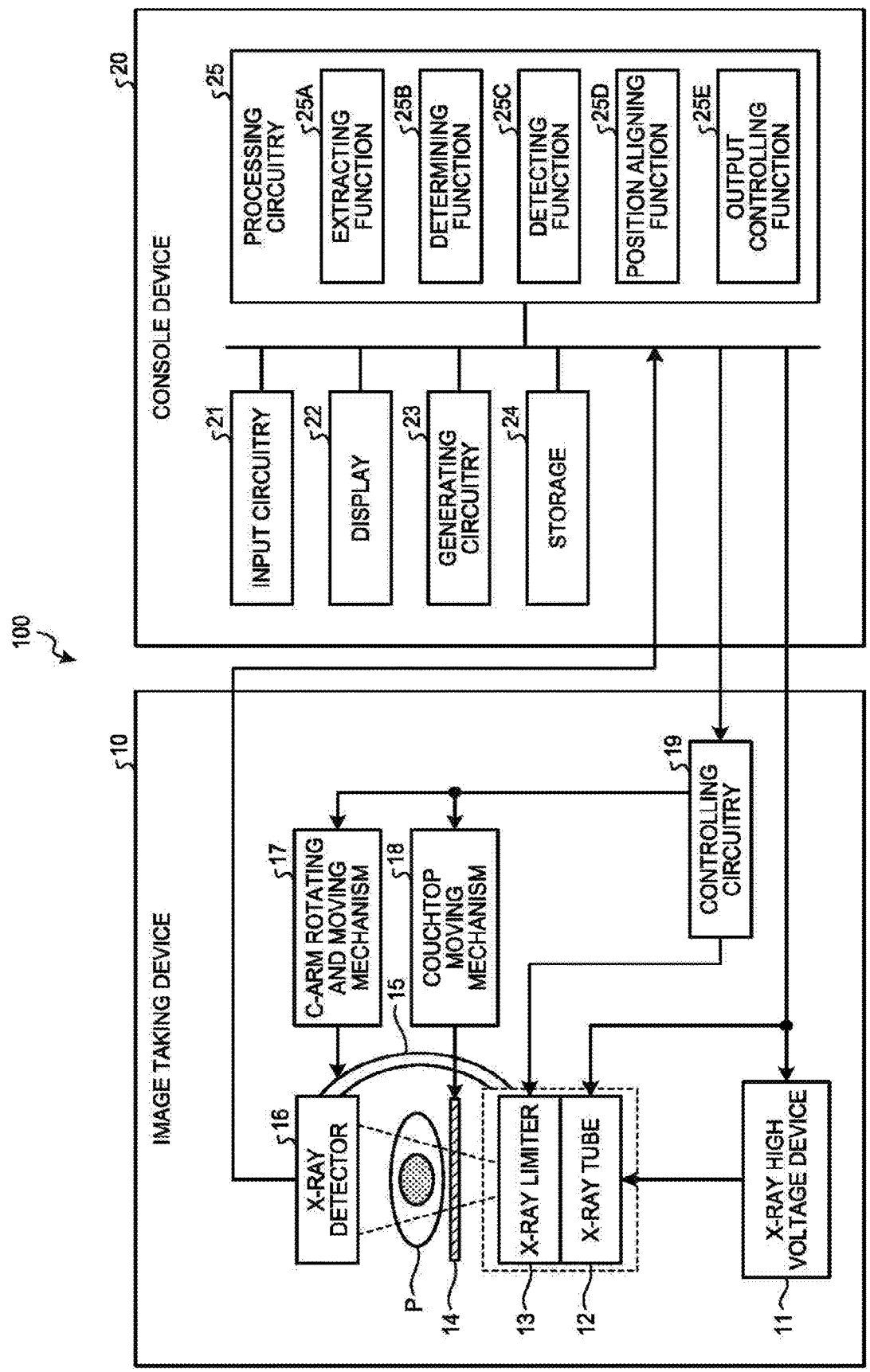

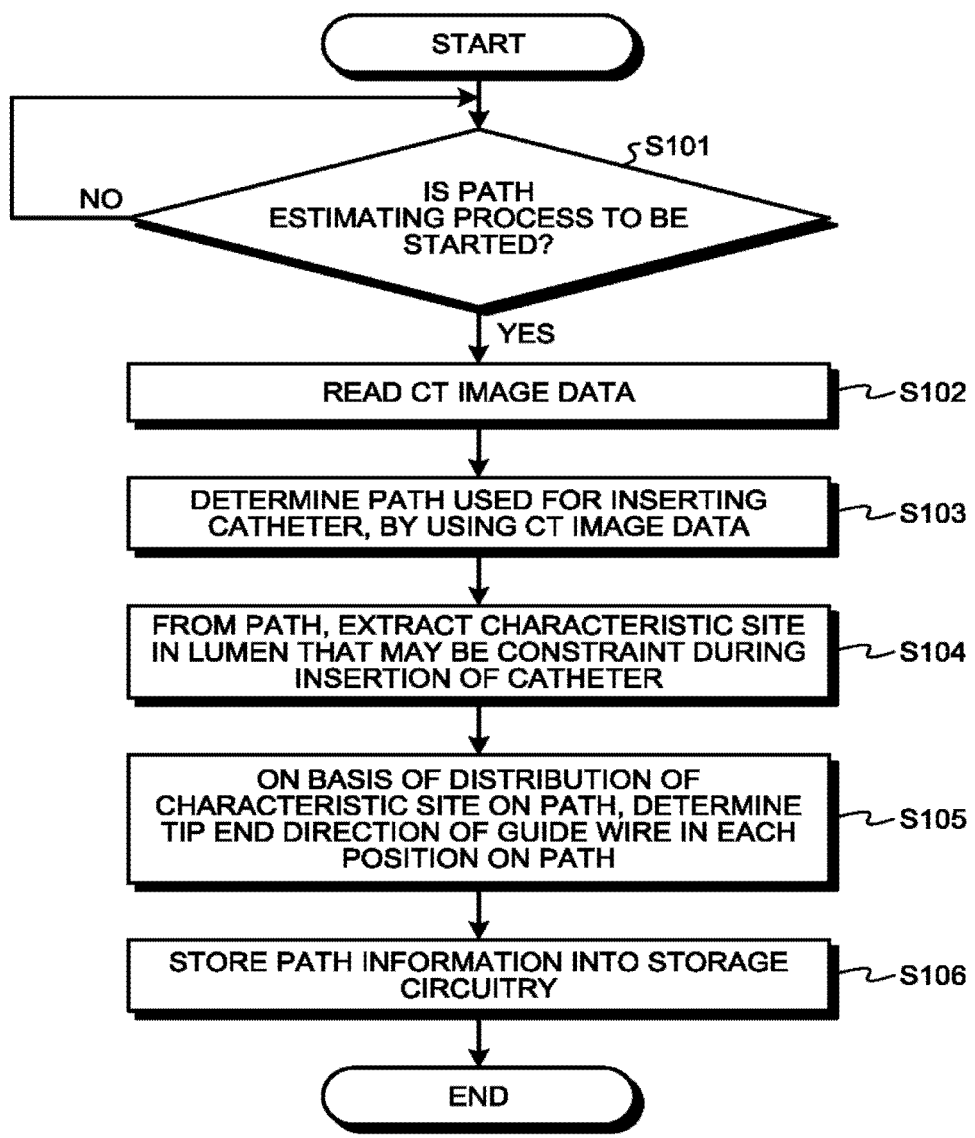

X-RAY DIAGNOSIS APPARATUS, MEDICAL IMAGE PROCESSING APPARATUS, MEDICAL IMAGE PROCESSING SYSTEM, AND MEDICAL IMAGE PROCESSING METHOD

CROSS-REFERENCE TO RELATED APPLICATIONS

This application is based upon and claims the benefit of priority from Japanese Patent Application No. 2017-198741, filed on Oct. 12, 2017; and Japanese Patent Application No. 2018-152591, filed on Aug. 14, 2018, the entire contents of which are incorporated herein by reference.

FIELD

Embodiments described herein relate generally to an X-ray diagnosis apparatus, a medical image processing apparatus, a medical image processing system, and a medical image processing method.

BACKGROUND

Conventionally, during treatment (surgery) procedures using a catheter, it is common for a practitioner to implement manipulations while viewing the position of the catheter in an X-ray image (a fluoroscopic image) taken by an X-ray diagnosis apparatus. Further, various techniques have been proposed to assist medical doctors in the implementations of the manipulations.

Examples of the techniques for assisting operators (medical doctors) during treatment procedures using a catheter include a technique by which a simulation is performed in advance to calculate a path used for inserting the catheter to a targeted site. For example, according to this technique, a blood vessel structure on the inside of the examined subject is extracted from three-dimensional CT image data taken by an X-ray Computed Tomography (CT) apparatus, so as to determine an appropriate path through a blood vessel leading to the targeted site. The determined path is presented to the operator when a catheter treatment procedure is carried out. The operator is able to guide the catheter to the targeted site, while viewing the presented path on a screen.

BRIEF DESCRIPTION OF THE DRAWINGS

FIG. 1 is a block diagram illustrating an exemplary configuration of an X-ray diagnosis apparatus according to a first embodiment;

FIG. 3 is a flowchart illustrating a processing procedure of a path estimating process performed by the X-ray diagnosis apparatus according to the first embodiment;

DETAILED DESCRIPTION

Figure 2A:
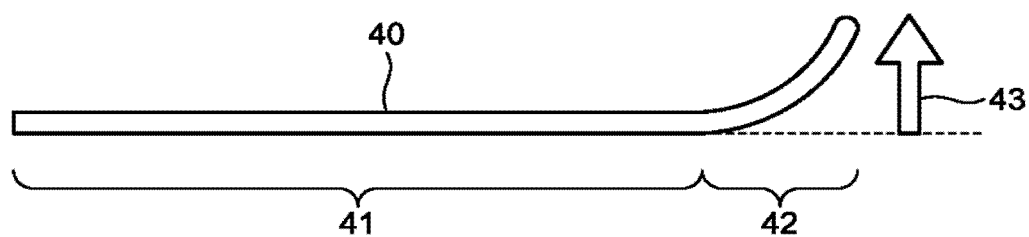
FIGS. 2A and 2B are drawings illustrating examples of the shape of a tip end part of a guide wire according to the first embodiment.

An X-ray diagnosis apparatus according to an embodiment includes processing circuitry. The processing circuitry is configured to extract a characteristic site in a lumen that may be a constraint during insertion of a surgical device, from medical image data used for determining a path through which the surgical device is to be inserted. On the basis of the characteristic site, the processing circuitry is configured to determine a tip end direction defined in accordance with a curved shape of a tip end part of the surgical device, in each of a plurality of positions on the path. The processing circuitry is configured to output path information including the tip end direction in each of the positions on the path.

Exemplary embodiments of an X-ray diagnosis apparatus, a medical image processing apparatus, a medical image processing system, and a medical image processing computer program will be explained, with reference to the drawings. Possible embodiments are not limited to those described below. Further, the description of each of the embodiments is, in principle, similarly applicable to any other embodiment.

First Embodiment

To begin with, an exemplary configuration of an X-ray diagnosis apparatus 100 according to a first embodiment will be explained, with reference to FIG. 1. FIG. 1 is a block diagram illustrating the exemplary configuration of the X-ray diagnosis apparatus 100 according to the first embodiment.

As illustrated in FIG. 1, the X-ray diagnosis apparatus 100 includes an image taking device 10 and a console device 20. The image taking device 10 and the console device 20 are connected so as to be able to communicate with each other.

The image taking device 10 includes an X-ray high voltage device 11, an X-ray tube 12, an X-ray limiter 13, a couchtop 14, a C-arm 15, an X-ray detector 16, a C-arm rotating and moving mechanism 17, a couchtop moving mechanism 18, and controlling circuitry 19. The X-ray high voltage device 11, the X-ray tube 12, the X-ray limiter 13, the couchtop 14, the C-arm 15, the X-ray detector 16, the C-arm rotating and moving mechanism 17, the couchtop moving mechanism 18, and the controlling circuitry 19 are connected, as necessary, so as to be able to communicate with one another.

The X-ray high voltage device 11 is a high-voltage power supply configured, under control of processing circuitry 25 (explained later), to generate high voltage and to supply the generated high voltage to the X-ray tube 12. For example, the X-ray high voltage device 11 is configured by using an inverter circuit, a high-voltage transformer configured to generate the high voltage, a high-voltage rectifying circuit, and the like.

The X-ray tube 12 is a device configured to generate X-rays by using the high voltage supplied thereto from the X-ray high voltage device 11. The X-ray tube 12 is structured with a vacuum tube configured to emit thermo electrons from a negative pole (a filament) toward a positive pole (a target), by receiving the supply of the high voltage from the X-ray high voltage device 11.

The X-ray limiter 13 is a member configured to limit the X-rays generated by the X-ray tube 12 so as to be selectively radiated onto an imaging target region of an examined subject (hereinafter, "patient") P, under control of the controlling circuitry 19 (explained later). For example, the X-ray limiter 13 is configured by using limiting blades and a filter. The limiting blades may be, for example, four plate-like slidable members. When being slid by the controlling circuitry 19, the limiting blades limit the X-rays generated by the X-ray tube 12. Further, the filter is an X-ray filter used for adjusting (attenuating) the X-rays radiated onto the patient P. For example, the filter is configured to adjust the X-rays generated by the X-ray tube 12, by changing the radiation quality of the X-rays passing therethrough, with the material and/or the thickness thereof.

The couchtop 14 is a bed on which the patient P is placed and is arranged over a couch (not illustrated). It should be noted that the patient P is not included in the X-ray diagnosis apparatus 100.

The C-arm 15 is a supporting member configured to support the X-ray tube 12, the X-ray limiter 13, and the X-ray detector 16. The X-ray tube 12 with the X-ray limiter 13 and the X-ray detector 16 are arranged by the C-arm 15 so as to oppose each other while the patient P is interposed therebetween.

The X-ray detector 16 includes detecting elements arranged in a matrix formation and is configured to detect X-rays that have passed through the patient P. For example, the X-ray detector 16 includes, as the detecting elements, Complementary Metal Oxide Semiconductor (CMOS) elements or Charge Coupled Devices (CCDs). The detecting elements are configured to convert the X-rays that have passed through the patient P into electrical signals, to accumulate the electrical signals therein, and to transmit the accumulated electrical signals to generating circuitry 23.

The C-arm rotating and moving mechanism 17 is a motive power mechanism used for rotating and moving the C-arm 15. For example, the C-arm rotating and moving mechanism 17 is configured to rotate and move the C-arm 15 by using motive power generated by an actuator such as a motor.

The couchtop moving mechanism 18 is a motive power mechanism used for moving the couchtop 14. For example, the couchtop moving mechanism 18 is configured to move the couchtop 14 by using motive power generated by an actuator.

The controlling circuitry 19 is an electronic circuit configured to control operations of the image taking device 10. For example, under the control of the processing circuitry 25, the controlling circuitry 19 is configured to control the C-arm rotating and moving mechanism 17 and the couchtop moving mechanism 18. For example, the controlling circuitry 19 is configured to adjust the rotating and the moving of the C-arm 15 and the moving of the couchtop 14, by controlling the C-arm rotating and moving mechanism 17 and the couchtop moving mechanism 18.

Further, under the control of the processing circuitry 25, the controlling circuitry 19 is configured to control operations of the X-ray limiter 13. For example, by sliding the limiting blades included in the X-ray limiter 13, the controlling circuitry 19 is configured to control the radiation range of the X-rays radiated onto the patient P. Further, by adjusting the position of the filter included in the X-ray limiter 13, the controlling circuitry 19 is configured to control the distribution of doses of the X-rays radiated onto the patient P.

Further, the console device 20 includes input circuitry 21, a display 22, the generating circuitry 23, storage 24, and the processing circuitry 25. The input circuitry 21, the display 22, the generating circuitry 23, the storage 24, and the processing circuitry 25 are connected so as to be able to communicate with one another.

The input circuitry 21 is realized by using a trackball, a switch button, a mouse, and/or a keyboard, used for inputting various types of instructions, various types of settings, and the like. The input circuitry 21 is connected to the processing circuitry 25 and is configured to convert an input operation received from an operator into an electrical signal and to output the electrical signal to the processing circuitry 25.

The display 22 is a display configured to display a Graphical User Interface (GUI) used for receiving instructions from the operator and one or more X-ray images. For example, the display 22 displays an X-ray image resulting from a filtering process performed by the processing circuitry 25.

The generating circuitry 23 is an electronic circuit configured to generate medical image data. For example, the generating circuitry 23 is configured to generate X-ray image data by using the electrical signals converted from the X-rays by the X-ray detector 16 and to store the generated X-ray image data into the storage 24. For example, the generating circuitry 23 generates the X-ray image data (e.g., a fluoroscopic image) by applying a current/voltage conversion, an Analog/Digital (A/D) conversion, and/or a parallel/serial conversion to the electrical signals received from the X-ray detector 16. After that, the generating circuitry 23 stores the generated X-ray image data into the storage 24. The generating circuitry 23 is an example of a generating unit.

The storage 24 is a storage device configured to receive and store therein the X-ray image data generated by the generating circuitry 23. Further, the storage 24 is configured to store therein the X-ray image data resulting from the filtering process performed by the processing circuitry 25. Also, the storage 24 is configured to store therein computer programs (hereinafter, "programs") that correspond to various types of functions and are executed as being read by the pieces of circuitry illustrated in FIG. 1.

The processing circuitry 25 is an electronic circuit configured to control overall operations of the X-ray diagnosis apparatus 100. For example, the processing circuitry 25 is configured to control the dose and the turning on and off of the X-rays radiated onto the patient P, by controlling the X-ray high voltage device 11 and adjusting the voltage supplied to the X-ray tube 12, according to an instruction from the operator transferred thereto from the input circuitry 21. Further, for example, the processing circuitry 25 is configured to adjust the rotating and the moving of the C-arm 15 and the moving of the couchtop 14 by controlling the controlling circuitry 19 according to an instruction from the operator. Further, the processing circuitry 25 is configured to control the distribution of doses of the X-rays by controlling the controlling circuitry 19. In addition, by controlling the generating circuitry 23, the processing circuitry 25 is configured to acquire the X-ray image data by controlling an image data generating process based on the electrical signals converted from the X-rays by the X-ray detector 16. Furthermore, the processing circuitry 25 is configured to cause the display 22 to display the X-ray image resulting from the filtering process and to cause the display 22 to display the GUI used for receiving instructions from the operator.

Further, for example, the processing circuitry 25 is configured to receive, via a network, medical image data (e.g., Computed Tomography (CT) image data, Magnetic Resonance Imaging (MRI) image data, or the like) acquired by a medical image diagnosis apparatus other than the X-ray diagnosis apparatus 100. Further, the processing circuitry 25 is configured to store the received medical image data into the storage 24. Further, the processing circuitry 25 is configured to cause the display 22 to display the received medical image data, together with the X-ray image data acquired by the X-ray diagnosis apparatus 100. The medical image data displayed in this situation may be an image resulting from an image processing process (a rendering process). Further, the medical image data displayed together with the X-ray image data may be obtained via a storage medium such as a Compact Disk Read-Only Memory (CD-ROM), a Magneto-Optical (MO) disk, a Digital Versatile Disk (DVD), or the like.

Further, the processing circuitry 25 executes an extracting function 25A, a determining function 25B, a detecting function 25C, a position aligning function 25D, and an output controlling function 25E. The extracting function 25A is an example of an extracting unit. The determining function 25B is an example of a determining unit. The detecting function 25C is an example of a detecting unit. The position aligning function 25D is an example of a position aligning unit. The output controlling function 25E is an example of an output controlling unit. Details of processes performed by the extracting function 25A, the determining function 25B, the detecting function 25C, the position aligning function 25D, and the output controlling function 25E executed by the processing circuitry 25 will be explained later.

In this situation, for example, the processing functions performed the constituent elements of the processing circuitry 25 illustrated in FIG. 1, namely, the extracting function 25A, the determining function 25B, the detecting function 25C, the position aligning function 25D, and the output controlling function 25E are recorded in the storage 24 in the form of computer-executable programs. The processing circuitry 25 is a processor configured to realize the functions corresponding to the programs by reading and executing the programs from the storage 24. In other words, the processing circuitry 25 that has read the programs has the functions illustrated within the processing circuitry 25 in FIG. 1.

Incidentally, during treatment procedures using a catheter, a guide wire may be inserted to precede the catheter, for the purpose of guiding the catheter to a targeted site. The guide wire is a tool (a surgical device) inserted into the body of a patient by passing through the inside of the catheter having a tubular structure. The guide wire is shaped so that a tip end part thereof is curved.

Figure 2B:
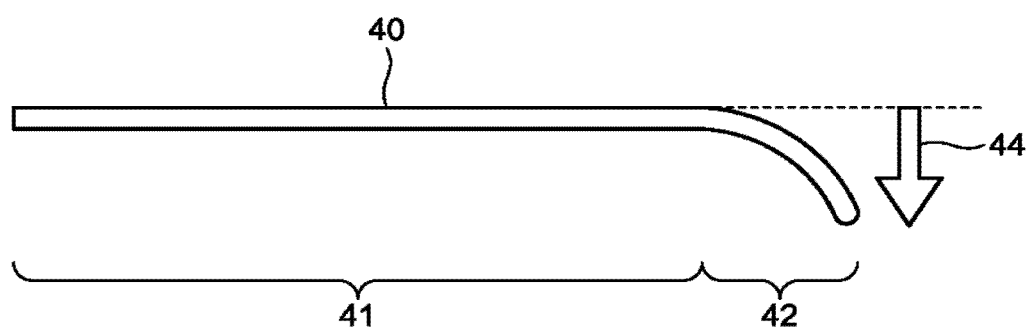

The shape of the tip end part of the guide wire will be explained, with reference to FIGS. 2A and 2B. FIGS. 2A and 2B are drawings illustrating examples of the shape of the tip end part of a guide wire according to the first embodiment. As illustrated in FIGS. 2A and 2B, a guide wire 40 includes a main body part 41 and a tip end part 42. The guide wire 40 is an example of the surgical device.

The main body part 41 is structured by using a material having flexibility to such an extent that the main body part 41 is able to change the shape thereof (to curve) according to the shape of the blood vessel into which the guide wire 40 is inserted. The main body part 41 is joined, at the tip end thereof, with the tip end part 42. The tip end part 42 is structured by using a material having strength (rigidity) to such an extent that shape memory is held. For example, before inserting a catheter into the patient P, the operator arranges the tip end part 42 to curve into an arbitrary shape. As a result, the guide wire 40 is shaped in such a manner that the tip end part is curved with respect to the axis (the central axis) thereof. Accordingly, even when being covered by the catheter, the tip end part 42 hardly changes the shape thereof and is able to maintain the curved shape defined by the operator.

In this situation, by using the curved shape of the tip end part 42, it is possible to define a "tip end direction" of the guide wire 40. For example, in FIG. 2A, the tip end part 42 is positioned upward with respect to the central axis (the part indicated with the broken line) of the main body part 41. In that situation, it is possible to define the tip end direction of the guide wire 40 as the direction indicated by an arrow 43 (the direction toward the top of the drawing). In contrast, in FIG. 2B, the tip end part 42 is positioned downward with respect to the central axis (the part indicated with the broken line) of the main body part 41. In that situation, it is possible to define the tip end direction of the guide wire 40 as the direction indicated by an arrow 44 (the direction toward the bottom of the drawing).

For example, the operator (a medical doctor) is able to advance the catheter in an arbitrary direction, by using the tip end direction of the guide wire 40. For example, the operator causes the guide wire 40 to advance in a blood vessel while preceding the catheter. When the guide wire 40 reaches a desired position such as a branching part of the blood vessel, the operator fixes the position of the guide wire 40 and inserts the catheter. The catheter that has been inserted advances in the blood vessel along the main body part 41, while remaining in the state of covering the main body part 41. After that, when having reached from the main body part 41 to the tip end part 42, the catheter advances while curving (changing the shape thereof) according to the shape of the tip end part 42.

For example, in the situation where the tip end direction of the guide wire 40 is an upward direction (the example in FIG. 2A), when the operator inserts the catheter, the catheter curves in the direction indicated by the arrow 43 according to the curved shape of the tip end part 42. In other words, by arranging the tip end direction of the guide wire 40 to be in the direction indicated by the arrow 43, the operator is able to cause the catheter to advance in the direction indicated by the arrow 43.

In contrast, in the situation where the tip end direction of the guide wire 40 is a downward direction (the example in FIG. 2B), when the operator inserts the catheter, the catheter curves in the direction indicated by the arrow 44 according to the curved shape of the tip end part 42. In other words, by arranging the tip end direction of the guide wire 40 to be in the direction indicated by the arrow 44, the operator is able to cause the catheter to advance in the direction indicated by the arrow 44.

As explained above, the operator is able to cause the catheter to advance in the direction extending along the tip end direction of the guide wire 40, by making use of the curved shape of the tip end part 42. With this arrangement, the operator is able to cause the catheter to advance in an arbitrary direction within the blood vessel that may curve or branch off in various directions. The operator is therefore able to guide the catheter to the targeted site.

However, when a catheter is to be guided in a blood vessel having complicated branches and being narrow such as a coronary artery, it is difficult for the operator to understand the direction of the branching part from X-ray image alone and to determine in which direction the tip end direction should be directed. In this situation, when guiding the catheter to a targeted site takes a long period of time, the X-ray exposure amount and the amount of a contrast agent to be administered will increase.

To cope with this situation, the X-ray diagnosis apparatus 100 according to the first embodiment executes the processing functions described below, for the purpose of assisting the catheter guiding process.

In the following sections, the term "tip end direction" will be used as defined with reference to FIGS. 2A and 2B; however, possible embodiments are not limited to this example. It is considered that the "tip end direction" can be defined in various ways; however, no matter how the tip end direction is defined, the applicability of the embodiments described herein shall not be affected.

For example, FIGS. 2A and 2B illustrate the examples in which the tip end direction is orthogonal to the direction (the part indicated with the broken line in the drawings) extending along the axial direction of the main body part 41; however, the tip end direction does not necessarily have to be orthogonal thereto. Because the operator is able to arbitrarily change the curved shape of the tip end part 42, when the operator arranges the tip end part to curve with a shallow angle, for example, the tip end direction may be defined as the shallow angle with respect to the direction extending along the axial direction. On the contrary, when the operator arranges the tip end part curve with a deep angle, the tip end direction may be defined as the deep angle with respect to the direction extending along the axial direction.

In other words, the tip end direction of the guide wire 40 explained in the present embodiment is the direction defined in accordance with the curved shape of the tip end part 42. More specifically, the tip end direction of the guide wire 40 is the direction intersecting the direction extending along the axial direction of the guide wire 40 (the main body part 41). That is to say, the tip end direction of the guide wire 40 is a direction that is presentable on a cross-sectional plane (e.g., an orthogonal cross-sectional plane 62, 65, or the like explained later) orthogonal to at least the axial direction of the main body part 41.

Further, the main body part 41 corresponds to a main axis part continuous with the tip end part 42. In other words, the guide wire 40 includes the main body part 41 serving as the main axis part and the tip end part 42. In this situation, the main body part 41 does not necessarily have to be in a linear shape. There is a high possibility that the main body part 41 will be arranged in the body of the patient while meandering so as to fit the shape of a tubular site in the body of the patient. In that situation, the tip end direction of the guide wire 40 is considered as a direction intersecting the direction (the extending direction) in which the main body part 41 (the main axis part) extends. In this situation, the direction in which the main body part 41 extends may be, for example, a direction obtained by mathematically extending the curved shape of the meandering main body part 41 or may be the direction of a line tangent to the main body part 41 at the joint part between the tip end part 42 and the main body part 41. Further, the direction in which the main body part 41 extends may be the extending direction of a blood vessel branch in which the guide wire 40 is inserted.

Next, in the first embodiment, a path estimating process and a guiding process will sequentially be explained. In this situation, the path estimating process is a simulation process to determine the tip end direction of the guide wire 40 in each of a plurality of positions on a path leading to a targeted site. Further, the guiding process is a process (a navigation process) of presenting an appropriate tip end direction of the guide wire 40 in accordance with the advancement of a catheter, for the purpose of assisting the guidance of the catheter.

The Path Estimating Process

First, the path estimating process will be explained. As the path estimating process, the X-ray diagnosis apparatus 100 executes processing functions as described below. In other words, the extracting function 25A extracts a characteristic site in a lumen that may be a constraint during the insertion of the guide wire 40, from three-dimensional medical image data used for determining a path through which the guide wire 40 is to be inserted, the guide wire 40 having the curved tip end part 42. Further, on the basis of the characteristic site, the determining function 25B determines a tip end direction defined in accordance with the curved shape of the tip end part 42, in each of the positions on the path.

In the first embodiment, an example will be explained in which the path estimating process is performed by the X-ray diagnosis apparatus 100 (the console device 20); however, possible embodiments are not limited to this example. For instance, the path estimating process may be performed in another medical image diagnosis apparatus such as an X-ray CT apparatus, an MRI apparatus, or the like. Alternatively, the path estimating process may be performed by a medical image processing apparatus such as a workstation.

The path estimating process performed by the X-ray diagnosis apparatus 100 according to the first embodiment will be explained, with reference to FIG. 3. FIG. 3 is a flowchart illustrating a processing procedure of the path estimating process performed by the X-ray diagnosis apparatus 100 according to the first embodiment. The processing procedure illustrated in FIG. 3 is started when an input is received from the operator indicating that the path estimating process should be started.

FIG. 3 will be explained with reference to FIGS. 4, 5A, 5B, 6A, 6B, 6C, and 7. FIGS. 4, 5A, 5B, 6A, 6B, 6C, and 7 are drawings for explaining the path estimating process performed by the X-ray diagnosis apparatus 100 according to the first embodiment.

In the explanation of the path estimating process below, an example will be explained in which the path estimating process is performed in CT image data; however, possible embodiments are not limited to this example. For instance, the X-ray diagnosis apparatus 100 is capable of performing the path estimating process, not only in CT image data, but also in three-dimensional medical image data obtained by imaging the patient P with an arbitrary medical image diagnosis apparatus. For example, the X-ray diagnosis apparatus 100 may perform the path estimating process in MR image data acquired by a Magnetic Resonance Imaging (MRI) apparatus.

At step S101, the processing circuitry 25 judges whether or not an input has been received from the operator indicating that a path estimating process should be started. For example, by using the input circuitry 21, the operator inputs information indicating that the path estimating process should be started. The input circuitry 21 outputs the information indicating that the path estimating process should be started and having been input by the operator, to the processing circuitry 25. When having received, from the input circuitry 21, the information indicating that the path estimating process should be started, the processing circuitry 25 determines that an input indicating that the path estimating process should be started has been received (step S101: Yes) and starts the processes at step S102 and thereafter. Conversely, until an input indicating that the path estimating process should be started is received (step S101: No), the processing circuitry 25 will not start the processes at step S102 and thereafter and remains in a standby state.

At step S102, the processing circuitry 25 reads CT image data. For example, the processing circuitry 25 reads the CT image data from the storage 24. In this situation, the CT image data may be, for example, image data obtained by an X-ray CT apparatus by imaging a region (e.g., the chest) including the heart of the patient P. When the CT image data is not stored in the storage 24, the processing circuitry 25 may obtain the CT image data from an X-ray CT apparatus or an external storage device used for storing therein medical image data that is connected via a network.

At step S103, the processing circuitry 25 determines a path used for inserting the catheter, by using the CT image data. In this situation, the determined path is information indicating a blood vessel (a blood vessel branch) used for inserting the catheter to the targeted site and is information that does not include the tip end direction of the guide wire 40 in each of the plurality of positions on the path. In other words, the process performed by the processing circuitry 25 in this situation is a process of identifying the blood vessel (the blood vessel branch) leading to the targeted site.

Figure 4:
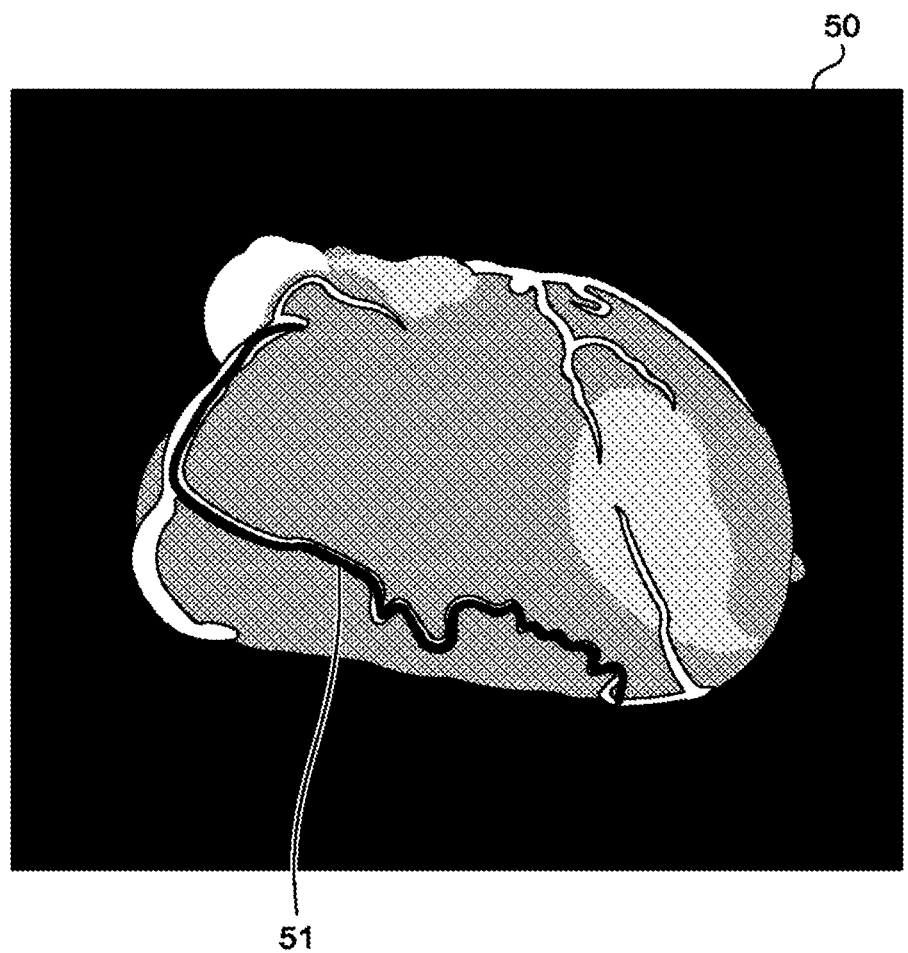
FIG. 4 is a drawing for explaining the path estimating process performed by the X-ray diagnosis apparatus according to the first embodiment.

For example, as illustrated in FIG. 4, by performing a segmentation process, the processing circuitry 25 extracts, from CT image data 50, the blood vessel structure of a coronary artery running through the body of the patient. In this situation, the blood vessel structure may be extracted, for example, as a structure constituted with a plurality of blood vessel branches. Further, the processing circuitry 25 determines a path 51 indicating the blood vessel (the blood vessel branch) leading to the targeted site designated by the operator. In this situation, the process of determining the path 51 leading to the targeted site is not limited to the process described above and may be implemented by using any of various conventional techniques.

In FIG. 4 and in the embodiments described below, an example is explained in which the catheter is inserted into a coronary artery; however, possible embodiments are not limited to this example. It is possible to apply the present embodiment to any treatment (surgery) procedure during which a catheter is inserted into an arbitrary tubular site into which catheters are insertable.

At step S104, from the path (e.g., the path 51 in FIG. 4), the extracting function 25A extracts a characteristic cite in the lumen that may be a constraint during the insertion of the catheter. For example, as the characteristic site, the extracting function 25A extracts at least one selected from among: a branching part and a curving part of the blood vessel into which the catheter is to be inserted; a structure formed in the blood vessel; and a part in which the blood vessel wall is thin.

For example, the extracting function 25A extracts, from the CT image data, a branching part, a curving part, a plaque, and a part in which the blood vessel wall is thin, by performing a pattern matching process that uses characteristics (characteristic information) in the image such as the branching part, the curving part, the plaque, and the part in which the blood vessel wall is thin. In this situation, the characteristic information used for the pattern matching process may be, for example, a template of a partial image region or information such as CT values corresponding to the characteristics and is stored in the storage 24 in advance. Further, in the present explanation, the plaque is used as an example of the structure; however, possible embodiments are not limited to this example. It is also possible to extract renal calculi, calcified sites, nerves, and the like in a similar manner.

At step S105, the determining function 25B determines the tip end direction of the guide wire 40 in each of the plurality of positions on the path, on the basis of the distribution of the characteristic site on the path. For example, when a branching part or a curving part has been extracted as the characteristic site, the determining function 25B determines the tip end direction in such a manner that the tip end part 42 of the guide wire 40 is directed in the advancing direction. As another example, when a structure (e.g., a plaque) or a part in which the blood vessel wall is thin has been extracted as the characteristic site, the determining function 25B determines the tip end direction in such a manner that the guide wire 40 will not touch the structure or the part in which the blood vessel wall is thin.

Figure 5A:
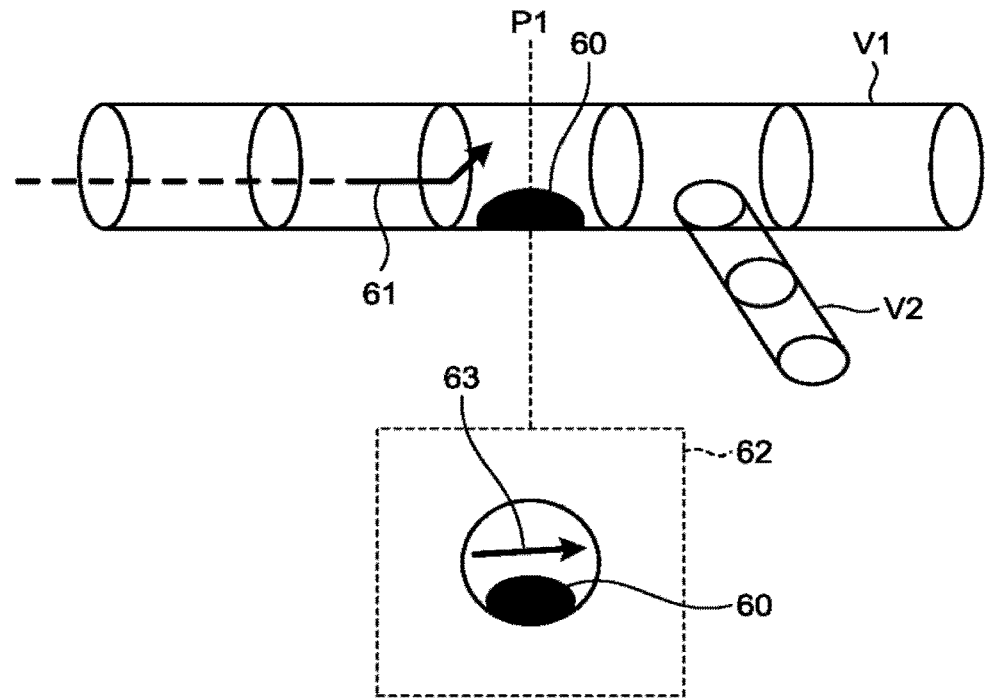
FIGS. 5A and 5B are more drawings for explaining the path estimating process performed by the X-ray diagnosis apparatus according to the first embodiment.
Figure 5B:
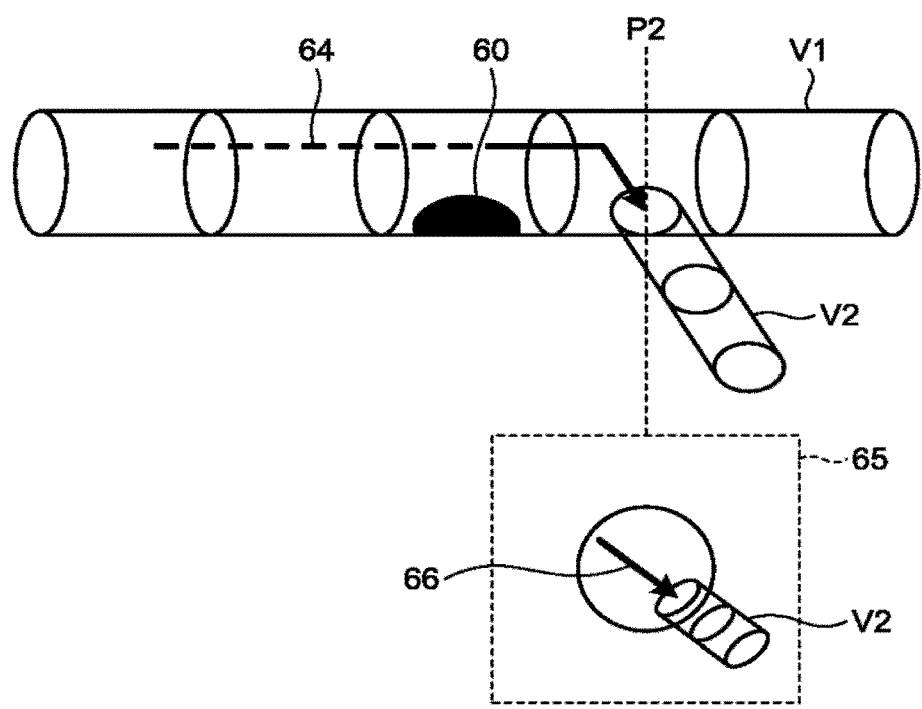

Next, a process performed in a situation where advancement is made into a branching blood vessel while avoiding a plaque will be explained, with reference to FIGS. 5A and 5B. FIGS. 5A and 5B illustrate an example in which a plaque 60 is present in a position P1 of a blood vessel branch V1, and the blood vessel branch V1 branches off as a blood vessel branch V2 at a position P2. In FIGS. 5A and 5B, the top of the drawing may be defined as the upper direction in terms of the vertical direction in the actual space or may be defined as the direction where the head of the patient P is present.

As illustrated in FIG. 5A, when the plaque 60 is present, the guide wire 40 is inserted so as not to touch the plaque 60, as indicated by an arrow 61. Accordingly, the determining function 25B determines the tip end direction of the guide wire 40 to be the direction indicated by an arrow 63, on an orthogonal cross-sectional plane 62 of the blood vessel branch V1 in the position P1.

In a specific example, the determining function 25B determines the tip end direction of the guide wire 40, by using the dimension of the width of the tip end part 42. The dimension of the width of the tip end part 42 corresponds, for example, to the length of the long axis of a projection image obtained by projecting the shape of the tip end part 42 onto a cross-sectional plane orthogonal to the axial direction of the guide wire 40. In this situation, the length of the arrow 63 corresponds to the dimension of the width of the tip end part 42. Further, the tip end (the arrowhead) of the arrow 63 corresponds to the tip end of the tip end part 42. Also, the tail end (the end opposite from the tip end) of the arrow 63 corresponds to the back side part (the part corresponding to the joint part between the tip end part 42 and the main body part 41) of the tip end part 42.

In one example, on the orthogonal cross-sectional plane 62, the determining function 25B determines the position of the arrow 63 in such a manner that the arrow 63 is arranged in the farthest position from the blood vessel wall of the blood vessel branch V1 and the plaque 60. After that, the determining function 25B determines the tip end direction of the guide wire 40 to be the direction indicated by the determined arrow 63.

In the example illustrated in FIG. 5A, the operator arranges the tip end direction of the guide wire 40 to be directed in the direction indicated by the arrow 63, before the tip end position of the guide wire 40 reaches the position P1. After that, the operator advances the guide wire 40 past the position P1, while keeping the tip end direction of the guide wire 40 directed in the direction indicated by the arrow 63. As a result, the operator is able to advance the guide wire 40 while avoiding the plaque 60.

Possible methods for determining the direction of the arrow 63 are not limited to the method described above. For example, it is also acceptable to determine the direction of the arrow 63 on the basis of the positional relationship with the plaque 60. For example, in FIG. 5A, because the plaque 60 is positioned at the bottom of the blood vessel branch V1, it is also acceptable to determine a direction (i.e., the horizontal direction) obtained by rotating 90 degrees from the direction where the plaque 60 is positioned, to be the tip end direction of the guide wire 40.

Subsequently, as illustrated in FIG. 5B, when the catheter is to be inserted into a blood vessel branch V2 branching off from the blood vessel branch V1, the guide wire 40 is inserted toward the direction of the blood vessel branch V2, as indicated by an arrow 64. Accordingly, on the orthogonal cross-sectional plane 65 of the blood vessel branch V1 in the position P2, the determining function 25B determines the tip end direction of the guide wire 40, to be the direction indicated by an arrow 66.

In the example in FIG. 5B, in the position P2, the operator arranges the tip end direction of the guide wire 40 to be directed in the direction indicated by the arrow 66. After that, the operator inserts the catheter, while fixing the position of the guide wire 40. As a result, the operator is able to insert the catheter into the blood vessel branch V2. Although the explanation was omitted above, the determining function 25B is also able to assist the insertion of the catheter in the curving part similarly to the example of the branching part, by arranging the tip end direction of the guide wire 40 to be directed in the direction of the blood vessel branch, which is the advancing direction.

Figure 6A:
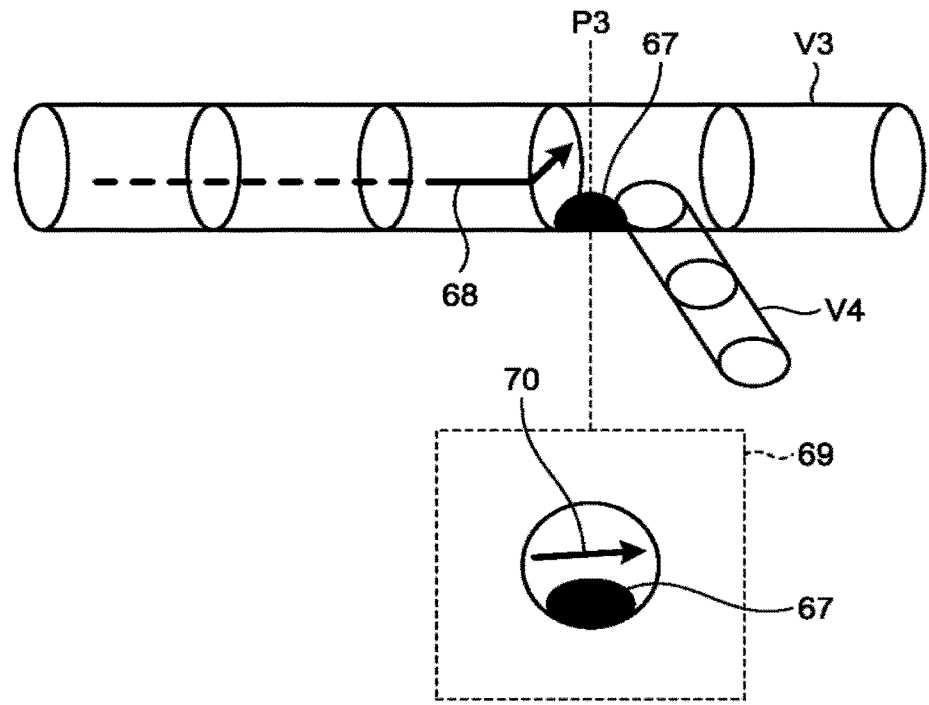
FIGS. 6A to 6C are other drawings for explaining the path estimating process performed by the X-ray diagnosis apparatus according to the first embodiment.
Figure 6B:
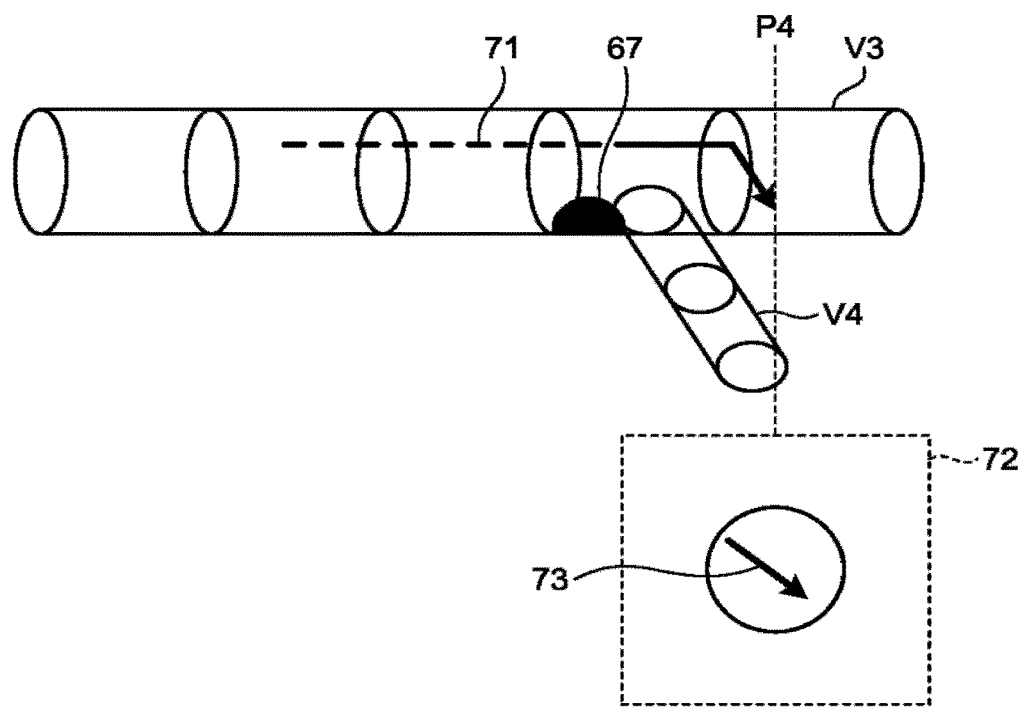
Figure 6C:
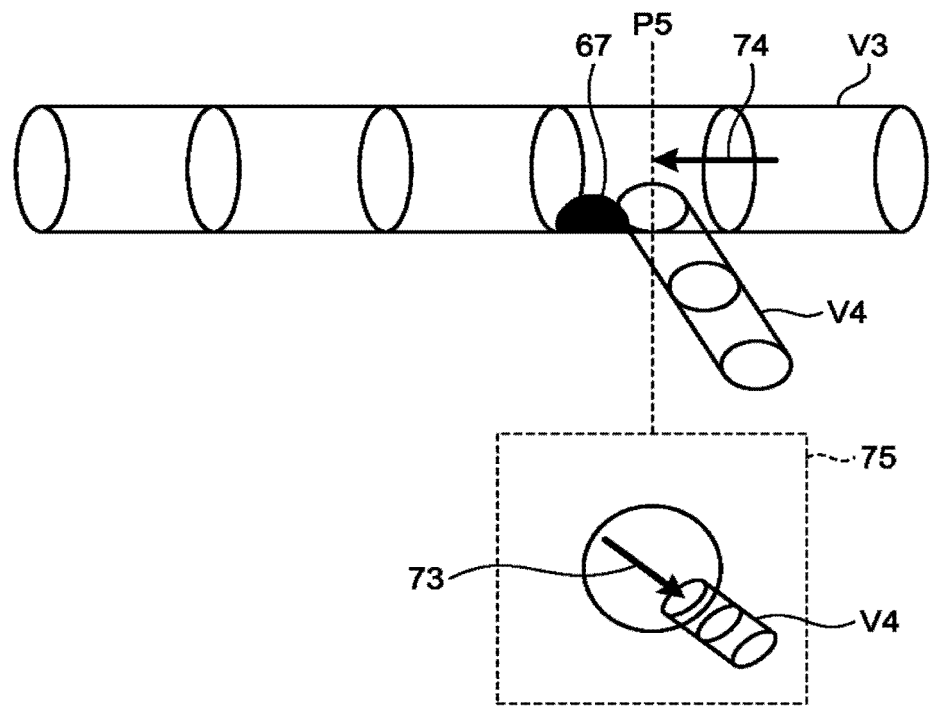

Next, a process performed when the plaque and a branching part are positioned close to each other will be explained, with reference to FIGS. 6A, 6B, and 6C. FIGS. 6A, 6B, and 6C illustrate an example in which a plaque 67 is present in a position P3 in a blood vessel branch V3, while the blood vessel branch V3 branches off as a blood vessel branch V4 at a position P5. In FIGS. 6A, 6B, and 6C, the top of the drawing may be defined as the upper direction in terms of the vertical direction in the actual space or may be defined as the direction where the head of the patient P is present.

As illustrated in FIG. 6A, when the plaque 67 is present, the guide wire 40 is inserted so as not to touch the plaque 67, as indicated by an arrow 68. Accordingly, the determining function 25B determines the tip end direction of the guide wire 40 to be the direction indicated by an arrow 70, on an orthogonal cross-sectional plane 69 of the blood vessel branch V3 in the position P3. The determining process in this situation is the same as the process explained with reference to FIG. 5A.

Subsequently, as illustrated in FIG. 6B, the determining function 25B guides the position of the tip end part 42 of the guide wire 40 to a position P4 that is sufficiently distant from the plaque 67, as indicated with an arrow 71. The reason is that, if the guide wire 40 was rotated near the plaque 67, there would be a possibility that the tip end part 42 might touch the plaque 67 by mistake. Accordingly, for example, when the distance between the position of the plaque 67 (the position P3) and the branching position (the position P5) off to the blood vessel branch V4 is smaller than a threshold value, the determining function 25B guides the position of the tip end part 42 to the position P4 that is sufficiently distant to such an extent that the possibility of touching the plaque 67 is considered to be low. Further, the determining function 25B determines the tip end direction to be the direction indicated by an arrow 73, so that the tip end of the guide wire 40 is directed in the direction of the blood vessel branch V4, on an orthogonal cross-sectional plane 72 of the blood vessel branch V3 in the position P4.

Further, as illustrated in FIG. 6C, the determining function 25B guides the guide wire 40 to be pulled back to the position P5, as indicated by an arrow 74. As a result, the operator is able to guide the catheter to the blood vessel branch V4 branching off, as indicated on an orthogonal cross-sectional plane 75, while keeping low the possibility of the guide wire 40 touching the plaque 67.

Figure 7:
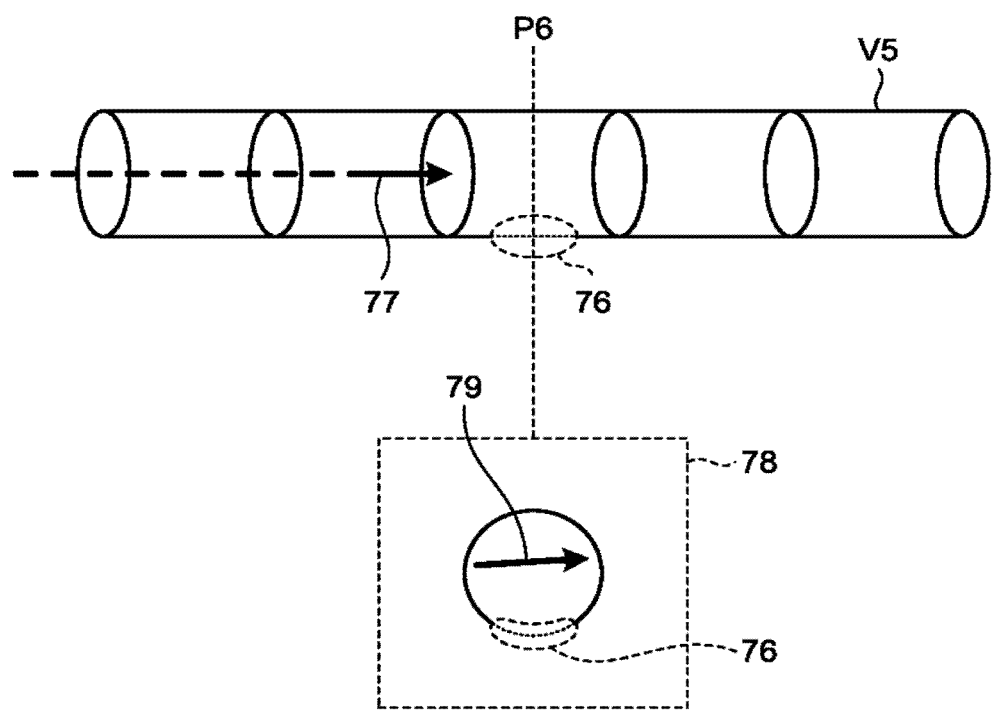
FIG. 7 is another drawing for explaining the path estimating process performed by the X-ray diagnosis apparatus according to the first embodiment.

Next, a process performed in the situation where advancement is made into a branching blood vessel while avoiding a part in which the blood vessel wall is thin will be explained, with reference to FIG. 7. FIG. 7 illustrates an example in which, in a position P6 of a blood vessel branch V5, a partial region 76 is present, which is a part in which the blood vessel wall is thin. In FIG. 7, the top of the drawing may be defined as the upper direction in terms of the vertical direction in the actual space or may be defined as the direction where the head of the patient P is present.

As illustrated in FIG. 7, when the partial region 76 is present in the forward direction of the guide wire 40 that has been advanced along an arrow 77, the determining function 25B determines the tip end direction of the guide wire 40 to be the direction indicated by an arrow 79, on an orthogonal cross-sectional plane 78 of the blood vessel branch V5 in the position P6. In this situation, the length of the arrow 79 corresponds to the dimension of the width of the tip end part 42. Further, the tip end (the arrowhead) of the arrow 79 corresponds to the tip end of the tip end part 42. Also, the tail end (the end opposite from the tip end) of the arrow 79 corresponds to the back side part (the part corresponding to the joint part between the tip end part 42 and the main body part 41) of the tip end part 42.

In one example, on the orthogonal cross-sectional plane 78, the determining function 25B determines the position of the arrow 79 in such a manner that the tip end part 42 of the guide wire 40 is arranged in the farthest position from the partial region 76. After that, the determining function 25B determines the tip end direction of the guide wire 40 to be the direction indicated by the determined arrow 79.

In the example illustrated in FIG. 7, the operator arranges the tip end direction of the guide wire 40 to be directed in the direction indicated by the arrow 79, before the tip end position of the guide wire 40 reaches the position P6. After that, the operator advances the guide wire 40 past the position P6, while keeping the tip end direction of the guide wire 40 directed in the direction indicated by the arrow 79. As a result, the operator is able to advance the guide wire 40 while avoiding the partial region 76, which is the part in which the blood vessel wall is thin.

Possible methods for determining the direction of the arrow 79 are not limited to the method described above. For example, it is also acceptable to determine the direction of the arrow 79 on the basis of the positional relationship with the part in which the blood vessel wall is thin. For example, in FIG. 7, because the partial region 76 is positioned at the bottom of the blood vessel branch V5, it is also acceptable to determine a direction (i.e., the horizontal direction) obtained by rotating 90 degrees from the direction where the partial region 76 is positioned, to be the tip end direction of the guide wire 40. In other words, as the tip end direction, the determining function 25B determines the angle (the direction) of the axial rotation defined in accordance with the curved shape of the tip end part 42. In this situation, for example, the angle of the axial rotation indicates a direction around the axis (the central axis) and can be expressed as an angle that uses a certain representative direction (the vertical direction or the horizontal direction) as a reference (0 degrees).

As explained above, the determining function 25B determines the tip end direction of the guide wire 40 in each of the plurality of positions on the path, on the basis of the characteristic site on the path. The processes of determining the tip end direction explained with reference to FIGS. 5A, 5B, 6A, 6B, 6C, and 7 are merely examples, and possible implementations of the processes are not limited those explained above.

Returning to the description of FIG. 3, at step S106, the output controlling function 25E stores the path information including the tip end direction of the guide wire 40 in each of the positions on the path, into the storage 24. For example, as the path information, the output controlling function 25E stores, into the storage 24, information including the information indicating the path 51 and the information indicating the tip end direction of the guide wire 40 in each of the plurality of positions on the path determined by the determining function 25B. The path information stored in the storage 24 is read as appropriate when necessary to be used in a guiding process (explained later). The path information may be referred to as "path guidance".

The Guiding Process

Next, the guiding process will be explained. As the guiding process, the X-ray diagnosis apparatus 100 executes the processing functions as described below. In other words, the detecting function 25C detects the tip end position and the tip end direction of a surgical device inserted in the patient, from an X-ray image. Further, the position aligning function 25D performs a position aligning process between the X-ray image and three-dimensional medical image data. On the basis of a result of the position aligning process, the output controlling function 25E arranges the tip end position and the tip end direction to be displayed in a rendering image based on the three-dimensional medical image data.

Figure 8:
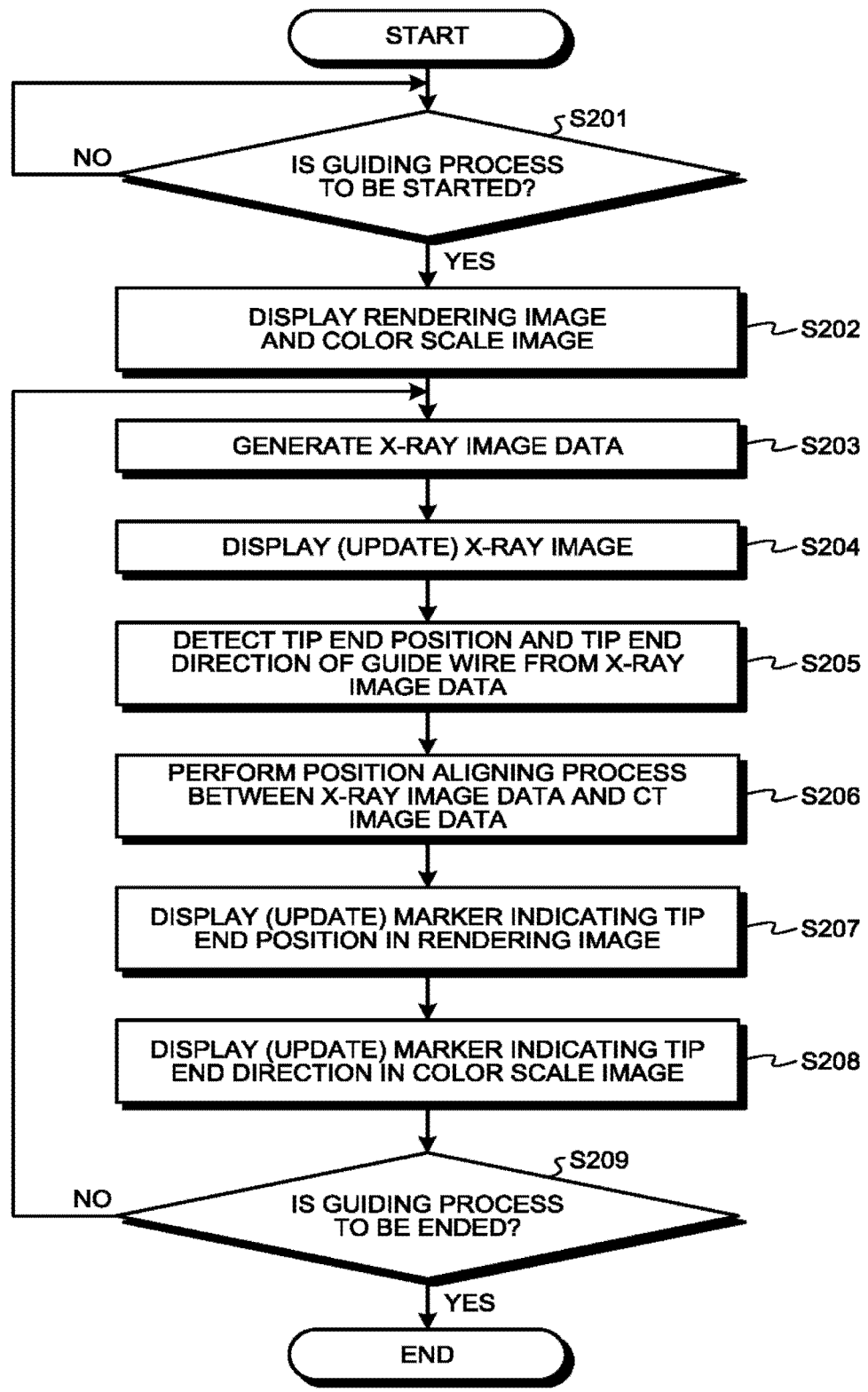
FIG. 8 is a flowchart illustrating a processing procedure in a guiding process performed by the X-ray diagnosis apparatus according to the first embodiment.
Figure 9:
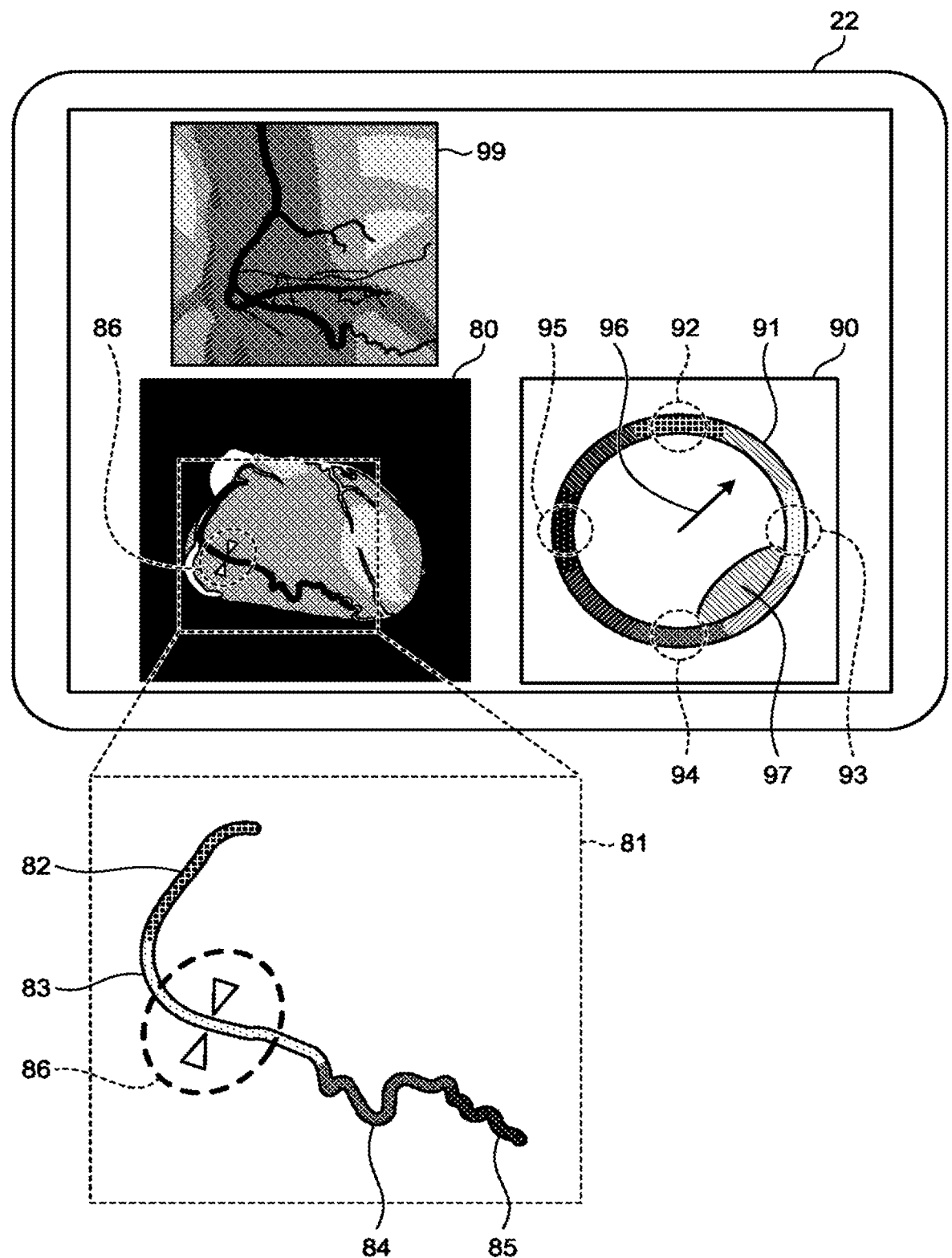
FIG. 9 is a drawing for explaining the guiding process performed by the X-ray diagnosis apparatus according to the first embodiment.

The guiding process performed by the X-ray diagnosis apparatus 100 according to the first embodiment will be explained, with reference to FIG. 8. FIG. 8 is a flowchart illustrating a processing procedure in the guiding process performed by the X-ray diagnosis apparatus 100 according to the first embodiment. The processing procedure illustrated in FIG. 8 is started when an input is received from the operator indicating that the guiding process should be started. FIG. 8 will be explained with reference to FIG. 9. FIG. 9 is a drawing for explaining the guiding process performed by the X-ray diagnosis apparatus 100 according to the first embodiment.

At step S201, the processing circuitry 25 judges whether or not an input has been received from the operator indicating that a guiding process should be started. For example, by using the input circuitry 21, the operator inputs information indicating that the guiding process should be started. The input circuitry 21 outputs the information indicating that the guiding process should be started and having been input by the operator, to the processing circuitry 25. When having received, from the input circuitry 21, the information indicating that the guiding process should be started, the processing circuitry 25 determines that an input indicating that the guiding process should be started has been received (step S201: Yes) and starts the guiding process at step S202 and thereafter. Conversely, until an input indicating that the guiding process should be started is received (step S201: No), the processing circuitry 25 will not start the guiding process at step S202 and thereafter and remains in a standby state.

At step S202, the output controlling function 25E causes a rendering image and a color scale image to be displayed. For example, as illustrated in FIG. 9, the output controlling function 25E causes the display 22 to display a rendering image 80 and a color scale image 90, on the basis of the path information determined in the path estimating process.

In this situation, as the path information, the output controlling function 25E causes the rendering image 80 to be displayed, the rendering image 80 being derived from three-dimensional medical image data in which pixel values corresponding to the tip end direction of the guide wire 40 is assigned to each of a plurality of positions on the path. For example, the rendering image 80 is a volume rendering image generated on the basis of CT image data. Further, the path 51 is rendered in the rendering image 80. As illustrated in an enlarged view 81, the path 51 includes partial regions 82, 83, 84, and 85. To each of the partial regions 82, 83, 84, and 85, pixel values corresponding to the tip end direction of the guide wire 40 are assigned. In this situation, the enlarged view 81 is an enlarged view of the path 51 contained in the rectangular region enclosed by the broken line rendered in the rendering image 80. Further, the rendering image 80 does not necessarily have to be a volume rendering image. The rendering image 80 may be an arbitrary rendering image such as a surface rendering image.

Further, the output controlling function 25E causes the color scale image 90 to be displayed, the color scale image 90 indicating directions corresponding to the pixel values. The color scale image 90 includes a ring-shaped region 91 in which the pixel values gradually change along the circumferential direction. The pixel values in the region 91 correspond to the pixel values assigned to the path in the rendering image 80 and serve as an index (a scale) indicating the tip end direction of the guide wire 40.

In FIG. 9, the pixel values of the partial region 82 are equal to the pixel values of a partial region 92 in the region 91. It is thus indicated that, when the tip end part 42 of the guide wire 40 is present in the partial region 82, it will be appropriate to arrange the tip end direction of the guide wire 40 to be directed in the direction indicated by the partial region 92 (the direction toward the top of the drawing). Further, the pixel values of the partial region 83 are equal to the pixel values of a partial region 93 in the region 91. It is thus indicated that, when the tip end part 42 of the guide wire 40 is present in the partial region 83, it will be appropriate to arrange the tip end direction of the guide wire 40 to be directed in the direction indicated by the partial region 93 (the direction toward the right-hand side of the drawing). Further, the pixel values of the partial region 84 are equal to the pixel values of a partial region 94 in the region 91. It is thus indicated that, when the tip end part 42 of the guide wire 40 is present in the partial region 84, it will be appropriate to arrange the tip end direction of the guide wire 40 to be directed in the direction indicated by the partial region 94 (the direction toward the bottom of the drawing). Further, the pixel values of the partial region 85 are equal to the pixel values of a partial region 95 in the region 91. It is thus indicated that, when the tip end part 42 of the guide wire 40 is present in the partial region 85, it will be appropriate to arrange the tip end direction of the guide wire 40 to be directed in the direction indicated by the partial region 95 (the direction toward the left-hand side of the drawing).

Further, the output controlling function 25E arranges a schematic drawing of the characteristic site to be displayed in the color scale image 90. For example, as illustrated in FIG. 9, when a plaque has been extracted from the CT image data in a position corresponding to the current tip end position of the guide wire 40, the output controlling function 25E arranges a plaque image 97 to be displayed in the position.

At step S203, the generating circuitry 23 generates the X-ray image data. For example, the generating circuitry 23 generates the X-ray image data on the basis of the X-rays detected by the X-ray detector 16. During treatment procedures using a catheter, a contrast-enhanced image is usually taken by enhancing the contrast of a blood vessel while using a contrast agent. It should be noted, however, that the applicability of the present embodiments shall not be affected by whether or not the contrast is enhanced.

At step S204, the output controlling function 25E causes the X-ray image to be displayed. For example, as illustrated in FIG. 9, the output controlling function 25E causes an X-ray image 99 to be displayed on the basis of the X-ray image data generated by the generating circuitry 23. In other words, the output controlling function 25E causes the X-ray image 99 to be displayed, together with the rendering image 80 and the color scale image 90. In this situation, when the X-ray image taking process (a fluoroscopy process) is performed in a real-time manner, the output controlling function 25E sequentially updates the display so that the display 22 displays the most up-to-date X-ray image.

At step S205, the detecting function 25C detects the tip end position and the tip end direction of the guide wire 40 from the X-ray image data. For example, by using a pattern matching process, the detecting function 25C detects the tip end position and the tip end direction of the guide wire 40 from the X-ray image data. In this situation, there are various techniques for detecting the tip end position and the tip end direction of the guide wire 40, by using an X-ray image projected from one direction, an X-ray image projected from two directions (e.g., a stereoscopic display image), or the like. The detecting function 25C may detect the tip end position and the tip end direction by using any of various conventional techniques.

At step S206, the position aligning function 25D performs a position aligning process between the X-ray image data and the CT image data. For example, the position aligning function 25D performs the position aligning process between the X-ray image data and the CT image data, by using a pattern matching process that uses patterns of structural characteristics of the blood vessels and the heart rendered in the X-ray image.

At step S207, the output controlling function 25E arranges a marker indicating the tip end position to be displayed in the rendering image. For example, as illustrated in FIG. 9, on the basis of a result of the position aligning process performed by the position aligning function 25D, the output controlling function 25E identifies, in the rendering image 80, a position corresponding to the current tip end position of the guide wire 40 detected by the detecting function 25C. After that, the output controlling function 25E arranges a marker 86 to be displayed in the identified position. In this situation, when the X-ray image taking process (a fluoroscopy process) is performed in a real-time manner, the output controlling function 25E sequentially updates the display so that the marker 86 is displayed in the most up-to-date position.

At step S208, the output controlling function 25E arranges a marker indicating the tip end direction to be displayed in a color scale image. For example, as illustrated in FIG. 9, on the basis of a result of the position aligning process performed by the position aligning function 25D, the output controlling function 25E identifies, in the color scale image 90, a direction corresponding to the current tip end direction of the guide wire 40 detected by the detecting function 25C. After that, the output controlling function 25E arranges a marker 96 to be displayed in the identified direction. In this situation, when the X-ray image taking process (a fluoroscopy process) is performed in a real-time manner, the output controlling function 25E sequentially updates the display so that the marker 96 is displayed in the most up-to-date direction.

In the example illustrated in FIG. 9, the marker 86 indicating the current tip end position is present in the partial region 83. The pixel values of the partial region 83 are approximately equal to the pixel values of the partial region 93 in the color scale image 90. Accordingly, the operator is able to understand that the appropriate tip end direction of the guide wire 40 in the current tip end position is the direction indicated by the partial region 93 (the direction toward the right-hand side of the drawing). More specifically, the operator is able to understand that it is necessary to rotate the current tip end direction indicated by the marker 96 toward the right.

At step S209, the processing circuitry 25 judges whether or not the guiding process should be ended. For example, the operator inputs information indicating that the guiding process should be ended, by using the input circuitry 21. The input circuitry 21 outputs the information indicating that the guiding process should be ended and having been input by the operator, to the processing circuitry 25. When having received, from the input circuitry 21, the information indicating that the guiding process should be ended, the processing circuitry 25 determines that the guiding process should be ended (step 3209: Yes) and ends the guiding process. On the contrary, until it is determined that the guiding process should be ended (step S209: No), the processing circuitry 25 returns to the process at step S203 and repeatedly performs the processes at steps S203 through S208.

The processing procedure illustrated in FIG. 8 is merely an example, and possible embodiments are not limited to this example. For instance, it is possible to modify the processing procedure described above as appropriate, as long as no conflict occurs in the processes performed in the processing.

The processes illustrated in FIG. 9 are merely examples, and possible embodiments are not limited to these examples. What is displayed on the display 22 is not limited to the examples illustrated in FIG. 9 and may be modified as appropriate. For example, although FIG. 9 illustrates the example in which the pixel values corresponding to the tip end direction of the guide wire 40 are rendered in the rendering image 80, the corresponding pixel values may be rendered in the X-ray image 99. In other words, the pixel values corresponding to the tip end direction of the guide wire 40 may be assigned to the position corresponding to the path 51 within the X-ray image 99.

Further, for example, the output controlling function 25E may display a blood vessel model. In this situation, the blood vessel model may be, for example, an illustration drawing of a blood vessel branch such as those in FIGS. 5A to 7. In the blood vessel model, it is possible to render, for example, any of the various types of objects explained with reference to FIGS. 5A to 7, such as an arrow (e.g., the arrow 61) indicating the advancing direction of the guide wire 40, the plaque 60, and the like.

As explained above, in the X-ray diagnosis apparatus 100 according to the first embodiment, the extracting function 25A is configured to extract the characteristic site in the lumen that may be a constraint during the insertion of the guide wire 40, from the three-dimensional medical image data used for determining the path through which the guide wire 40 of which the tip end part 42 is curved is to be inserted. Further, on the basis of the characteristic site, the determining function 25B is configured to determine the tip end direction defined in accordance with the curved shape of the tip end part 42 in each of the plurality of positions on the path. Further, the output controlling function 25E is configured to output the path information including the tip end direction in each of the plurality of positions on the path. With these arrangements, the X-ray diagnosis apparatus 100 is able to assist the catheter guiding process.

For example, even when guiding a catheter in a blood vessel having complicated branches and being narrow such as a coronary artery, the X-ray diagnosis apparatus 100 is able to present the tip end direction in accordance with the current tip end position of the guide wire 40. Accordingly, even when it is difficult for the operator to see, in the image, the blood vessel branches that are present in the advancing direction, the operator is able to insert the catheter in the correct advancing direction. Further, even when it is difficult for the operator to see, in the image, a plaque or a thin part, the operator is able to guide the catheter while avoiding the plaque or the thin part. Consequently, because the operator is able to guide the catheter to the targeted site in a shorter period of time, it is possible to reduce the X-ray exposure amount and the amount of the contrast agent to be administered.

First Modification Example of First Embodiment

It is possible to realize the present disclosure in various modes other than those explained in the above embodiment. For example, the processes at steps S205 through S208 explained with reference to FIG. 8 do not necessarily have to be performed. In that situation, the marker 86 and the marker 96 in FIG. 9 will not be displayed. However, the operator is able to understand the current tip end position of the guide wire 40 in the X-ray image 99. Accordingly, by comparing the X-ray image 99 with the rendering image 80, the operator is also able to roughly understand the current tip end position within the rendering image 80. After that, the operator is able to understand the pixel values corresponding to the current tip end position within the rendering image 80. Accordingly, by referring to the color scale image 90, the operator is also able to understand the current tip end direction corresponding to the pixel values. In that situation, the X-ray diagnosis apparatus 100 does not necessarily have to include the detecting function 25C and the position aligning function 25D.

Second Modification Example of First Embodiment

Further, for example, the X-ray diagnosis apparatus 100 may display, in the color scale image 90, a rotating direction of the guide wire 40 that is required to direct the detected current tip end direction toward an appropriate tip end direction.

For example, on the basis of the difference between the detected current tip end direction and the tip end direction included in the path information, the output controlling function 25E displays, in the color scale image 90, a marker indicating a rotating direction into which the guide wire 40 is to be rotated. More specifically, the output controlling function 25E calculates the rotation angle, by subtracting the current tip end direction (the angle) detected by the detecting function 25C from the tip end direction (the angle) corresponding to the tip end position read from the path information. On the basis of the sign (the positive or the negative) of the calculated rotation angle, the output controlling function 25E determines the rotating direction.

In this situation, when the guide wire 40 may, as a result of being rotated, touch a plaque or a part in which the blood vessel wall is thin, the determining function 25B may determine the rotating direction into which the guide wire 40 is to be rotated, in such a manner that the tip end part and the back side part of the tip end of the guide wire 40 will not touch the plaque or the part in which the blood vessel wall is thin. In contrast, when the guide wire 40 is not expected to touch a plaque or a part in which the blood vessel wall is thin, the determining function 25B may determine the rotating direction so as to keep small the angle by which the tip end direction is to be rotated.

Second Embodiment

For example, in a second embodiment, it is possible to arrange the heart rendered in the rendering image 80 to be displayed as if the heart was pulsating according to the heartbeats of the patient P.

For example, in the X-ray diagnosis apparatus 100 according to the second embodiment, the processing circuitry 25 obtains, from an X-ray CT apparatus, four-dimensional CT image data (which may be referred to as "4D CT image data") acquired by performing a dynamic volume scan (which may be referred to as a "dynamic scan") in which a plurality of pieces of volume data in a time series are taken. In this situation, the four-dimensional CT image data is image data including pieces of CT image data over a plurality of temporal phases corresponding to at least one heartbeat.

Further, the processing circuitry 25 performs a position aligning process among the pieces of CT image data corresponding to the plurality of temporal phases and being included in the four-dimensional CT image data. As a result, when path information has been determined by using a piece of CT image data corresponding to one temporal phase among the pieces of CT image data corresponding to the plurality of temporal phases, the processing circuitry 25 is able to apply the determined path information to the pieces of CT image data corresponding to the other temporal phases. In other words, in each of the rendering images corresponding to the plurality of temporal phases, the processing circuitry 25 is able to assign pixel values corresponding to the tip end direction of the guide wire 40 to each of a plurality of positions on the path.

Further, the output controlling function 25E displays rendering images corresponding to the plurality of temporal phases and being respectively generated from pieces of three-dimensional medical image data over the plurality of temporal phases that correspond to at least one heartbeat, while switching between the rendering images in accordance with an electrocardiographic signal of the patient P. For example, the output controlling function 25E receives the electrocardiographic signal from an electrocardiograph connected to the X-ray diagnosis apparatus 100. After that, the output controlling function 25E analyzes the received electrocardiographic signal and identifies the current cardiac temporal phase. Further, the output controlling function 25E causes the display 22 to display a rendering image of the piece of CT image data corresponding to the identified cardiac temporal phase. In this situation, no matter to which temporal phase the displayed rendering image corresponds, pixel values corresponding to the tip end direction of the guide wire 40 have been assigned to each of a plurality of positions on the path in the rendering image. As a result, the output controlling function 25E is able to display the heart rendered in the rendering image 80 illustrated in FIG. 9 as if the heart was pulsating according to the heartbeats of the patient P.

Other Embodiments

It is possible to carry out the present disclosure in various different modes other than those described in the above embodiments.

Using a Catheter

In the embodiments above, the examples are explained in which the tip end direction of the guide wire 40 is determined and in which the tip end direction of the guide wire 40 is presented; however, possible embodiments are not limited to these examples. For instance, when it is possible to define a tip end direction of a catheter, the X-ray diagnosis apparatus 100 is also capable of determining the tip end direction of the catheter and to present the tip end direction of the catheter.

A First Example of Using a Catheter

For example, known catheters include a catheter of a type (e.g., a guiding catheter) that is shaped so that a tip end part thereof is curved in advance. For a catheter of such a type, it is possible to define a tip end direction in the same manner as with the guide wire 40 explained above. For example, the tip end direction may be defined as the direction in which the tip end part is present with respect to the central axis of the catheter.

When a catheter of such a type that is shaped so that the tip end part thereof is curved in advance is being used, the X-ray diagnosis apparatus 100 performs a path estimating process and a guiding process. The path estimating process and the guiding process performed in this situation are the same as the path estimating process and the guiding process described above, except that the catheter is used in place of the guide wire 40.

Accordingly, when a catheter of such a type that is shaped so that the tip end part thereof is curved in advance is being used, the operator is able to understand which direction will be an appropriate direction for the curved tip end part of the catheter to be directed into.

A Second Example of Using a Catheter

Further, known catheters include a catheter of a type of which it is possible to freely arrange a tip end part to curve on the inside of a patient. For a catheter of such a type, it is possible to define the direction of the tip end part after being arranged to curve, as the tip end direction. For example, the determining function 25B determines the direction of the tip end part after being arranged to curve, as the tip end direction. More specifically, the determining function 25B defines the direction in which the tip end part is present with respect to the central axis of the catheter after the catheter is arranged to curve, as the tip end direction.

When a catheter of such a type of which it is possible to freely arrange the tip end part to curve on the inside of a patient is being used, the X-ray diagnosis apparatus 100 performs a path estimating process and a guiding process. The path estimating process and the guiding process performed in this situation are the same as the path estimating process and the guiding process described above, except that the catheter is used in place of the guide wire 40.

For example, as a result of the guiding process, the X-ray diagnosis apparatus 100 causes the display 22 to display the same display screen as the display screen illustrated in FIG. 9. In the example illustrated in FIG. 9, the marker 86 indicating the current tip end position is present in the partial region 83. The pixel values of the partial region 83 are approximately equal to the pixel values of the partial region 93 in the color scale image 90. Accordingly, the operator is able to understand that the appropriate tip end direction of the catheter in the current tip end position is the direction indicated by the partial region 93 (the direction toward the right-hand side of the drawing). In this situation, the operator arranges the tip end of the catheter to curve toward the right.

With these arrangements, when a catheter of such a type of which it is possible to freely arrange the tip end part to curve on the inside of a patient is being used, the operator is able to understand which direction will be an appropriate direction for the tip end part of the catheter to be curved into.

A Third Example of Using a Catheter

Further, known catheters include a catheter of a type of which it is possible to arrange the tip end part to curve into only a predetermined direction on the inside of a patient. For a catheter of such a type, it is possible to define the direction of the tip end part after being arranged to curve, as the tip end direction. For example, the determining function 25B determines the direction of the tip end part after being arranged to curve, as the tip end direction. More specifically, the determining function 25B defines the direction in which the tip end part is present with respect to the central axis of the catheter after the catheter is arranged to curve, as the tip end direction.

When a catheter of such a type of which it is possible to arrange the tip end part to curve into only a predetermined direction on the inside of a patient is being used, the X-ray diagnosis apparatus 100 performs a path estimating process and a guiding process. The path estimating process and the guiding process performed in this situation are the same as the path estimating process and the guiding process described above, except that the catheter is used in place of the guide wire 40.

For example, as a result of the guiding process, the X-ray diagnosis apparatus 100 causes the display 22 to display the same display screen as the display screen illustrated in FIG. 9. In the example illustrated in FIG. 9, the marker 86 indicating the current tip end position is present in the partial region 83. The pixel values of the partial region 83 are approximately equal to the pixel values of the partial region 93 in the color scale image 90. Accordingly, the operator is able to understand that the appropriate tip end direction of the catheter in the current tip end position is the direction indicated by the partial region 93 (the direction toward the right-hand side of the drawing). In this situation, the operator at first applies an axial rotation to the catheter so that the catheter becomes able to curve toward the right and subsequently arranges the tip end of the catheter to curve toward the right.

With these arrangements, when a catheter of such a type of which it is possible to arrange the tip end part to curve into only a predetermined direction on the inside of a patient is being used, the operator is able to understand which direction will be an appropriate direction for the tip end part of the catheter to be curved into.

A Medical Information Processing System

For example, the various types of processing functions explained in the above embodiments are applicable to a medical information processing system.

Figure 10:
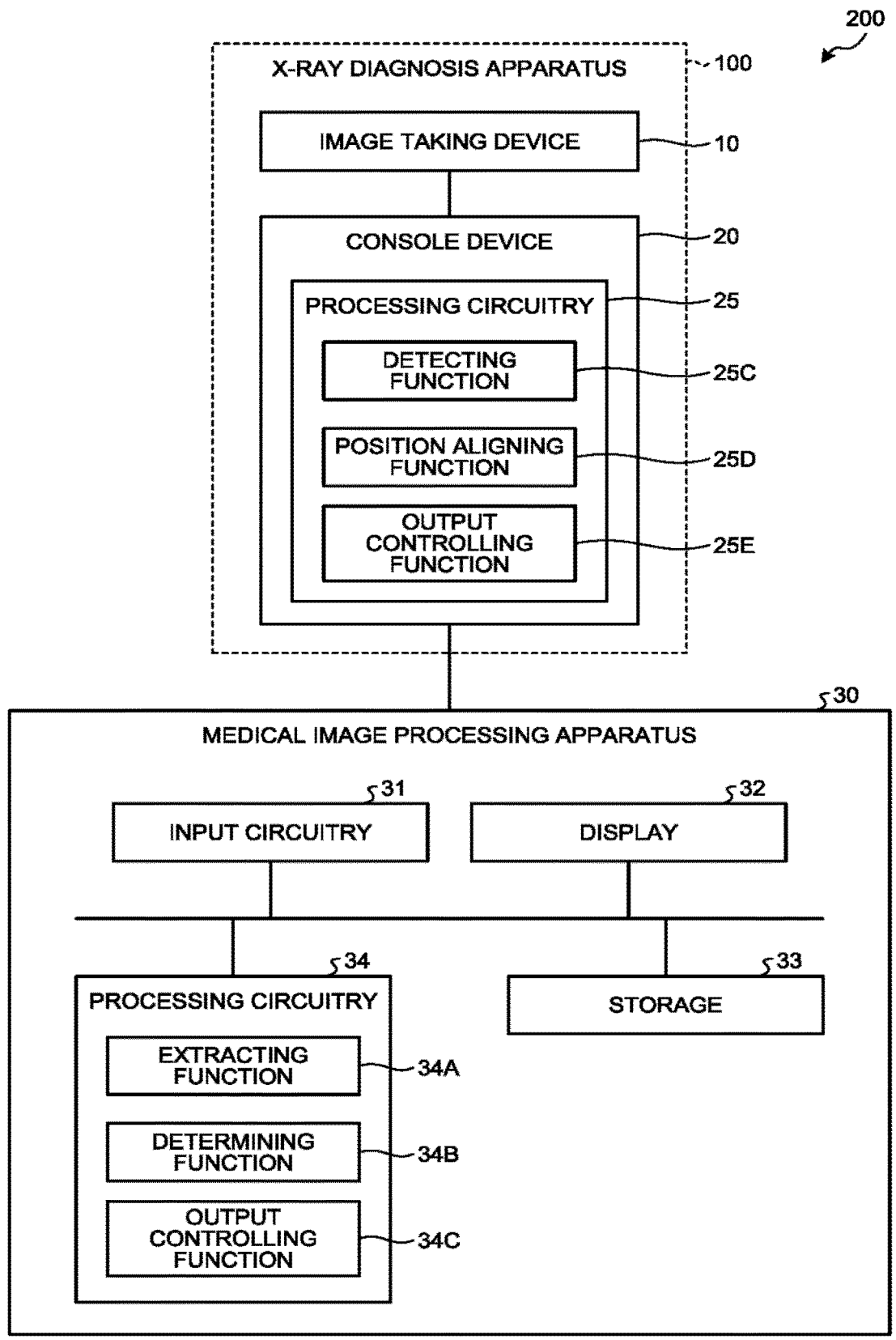
FIG. 10 is a block diagram illustrating an exemplary configuration of a medical information processing system according to another embodiment.

An exemplary configuration of a medical information processing system 200 according to another embodiment will be explained, with reference to FIG. 10. FIG. 10 is a block diagram illustrating the exemplary configuration of the medical information processing system 200 according to said another embodiment.

As illustrated in FIG. 10, the medical information processing system 200 includes an X-ray diagnosis apparatus 100 and a medical image processing apparatus 30. The X-ray diagnosis apparatus 100 and the medical image processing apparatus 30 are connected so as to be able to communicate with each other via a network.

In the X-ray diagnosis apparatus 100, the processing circuitry 25 is configured to execute, for example, the detecting function 25C, the position aligning function 25D, and the output controlling function 25E. Because the detecting function 25C, the position aligning function 25D, and the output controlling function 25E are the same as the detecting function 25C, the position aligning function 25D, and the output controlling function 25E explained in the first embodiment, the explanations thereof will be omitted. Further, because the configurations of the X-ray diagnosis apparatus 100 other than the configuration of the processing circuitry 25 are the same as those of the X-ray diagnosis apparatus 100 illustrated in FIG. 1, the explanations thereof will be omitted.

For example, the medical image processing apparatus 30 corresponds to an information processing apparatus such as a personal computer, a workstation, or the like or to a controlling device for a medical image diagnosis apparatus such as a console device or the like included in an X-ray CT apparatus. The medical image processing apparatus 30 includes input circuitry 31, a display 32, storage 33, and processing circuitry 34. The input circuitry 31, the display 32, the storage 33, and the processing circuitry 34 are connected so as to be able to communicate with one another.

The input circuitry 31 is an input device such as a mouse, a keyboard, a touch panel, and/or the like used for receiving various types of instructions and setting requests from the operator. The display 32 is a display configured to display a medical image and to display a GUI used by the operator for inputting the various types of setting requests via the input circuitry 31.

The storage 33 may be, for example, a Not AND (NAND) flash memory or a Hard Disk Drive (HDD) and is configured to store therein various types of programs used for displaying medical image data and the GUI as well as information used by the programs.

The processing circuitry 34 is an electronic device (a processor) configured to control overall processes performed by the medical image processing apparatus 30. The processing circuitry 34 is configured to execute an extracting function 34A, a determining function 34B, and an output controlling function 34C. The processing functions executed by the processing circuitry 34 are recorded in the storage 33 in the form of computer-executable programs. By reading and executing the programs, the processing circuitry 34 realizes the functions corresponding to the read programs.

For example, the extracting function 34A is capable of executing the same processes, in principle, as those executed by the extracting function 25A illustrated in FIG. 1. In other words, from the three-dimensional medical image data used for determining the path through which the guide wire 40 of which the tip end part 42 is curved is to be inserted, the extracting function 34A is configured to extract a characteristic site in the lumen that may be a constraint during the insertion of the guide wire 40. Further, the determining function 34B is capable of executing the same processes, in principle, as those executed by the determining function 25B illustrated in FIG. 1. In other words, on the basis of the characteristic site, the determining function 34B is configured to determine a tip end direction defined in accordance with the curved shape of the tip end part 42 in each of a plurality of positions on the path. Further, the output controlling function 34C is capable of executing the same processes, in principle, as those executed by the output controlling function 25E illustrated in FIG. 1. In other words, the output controlling function 34C is configured to store path information including the tip end direction of the guide wire 40 in each of the positions on the path, into the storage 24.

In other words, by employing the extracting function 34A, the determining function 34B, and the output controlling function 34C, the medical image processing apparatus 30 is configured to perform the path estimating process illustrated in FIG. 3. After that, the medical image processing apparatus 30 transmits the path information determined in the path estimating process to the X-ray diagnosis apparatus 100. On the basis of the path information transmitted thereto by the medical image processing apparatus 30, the X-ray diagnosis apparatus 100 performs the guiding process illustrated in FIG. 8. Accordingly, the medical information processing system 200 is able to assist the catheter guiding process.

Determining a Path in Accordance with the Amount of a Contrast Agent

Further, for instance, the example was explained in which, at step S103, the path is determined in one-to-one correspondence with the targeted site; however, possible embodiments are not limited to this example. For instance, for a coronary artery, as a result of a blood vessel bypass being formed due to a stenosis or the like, there is a possibility that a plurality of paths leading to a targeted site may be present. In that situation, the processing circuitry 25 may calculate the amount of contrast agent to be used with respect to each of the paths so as to select the path that will use the smallest amount of contrast agent. In that situation, the processing circuitry 25 calculates the diameter and the length of the blood vessel branch included in each of the paths from CT image data and further calculates the amount of contrast agent to be used, by obtaining the volume of the blood vessel for each of the paths by calculating "the diameter×the length".

Combining a Display of a Virtual Endoscope

Further, for example, it is possible to combine the present disclosure with a display of a virtual endoscope.

For example, on the basis of CT image data, the output controlling function 25E generates projection image data in which the interior of the lumen is projected by using the tip end position as a viewpoint. More specifically, the output controlling function 25E generates the projection image data by performing a projecting process while using the tip end position detected by the detecting function 25C as the viewpoint and using the advancing direction of the guide wire 40 as a line-of-sight direction. After that, the output controlling function 25E arranges the generated projection image data to be displayed on the inner circumferential side of the color scale image 90 illustrated in FIG. 9. More specifically, the output controlling function 25E arranges the projection image data to be displayed so as to be superimposed on the inner circumferential side of the ring-shaped region 91. As a result, the operator is able to browse an image as if he/she was viewing the advancing direction from the tip end position of the guide wire 40 by using an endoscope. Further, the operator is able to view, in the projection image, the marker 96 indicating an appropriate tip end direction. The operator is therefore able to easily understand the appropriate tip end direction.

Using a Bi-Plane Imaging Method

In the above embodiments, the examples were explained in which the three-dimensional medical image data (the CT image data) is used; however, possible embodiments are not limited to these examples. For instance, it is also acceptable to use bi-plane image data taken by using a bi-plane imaging method.

For example, the X-ray diagnosis apparatus 100 acquires frontal-side image data and lateral-side image data, as the bi-plane image data. After that, by using the frontal-side image data and the lateral-side image data, the X-ray diagnosis apparatus 100 performs the path estimating process and the guiding process explained above. Accordingly, the X-ray diagnosis apparatus 100 is able to assist the catheter guiding process.

In this situation, the image data is not necessarily limited to the frontal-side image data and the lateral-side image data. For instance, the X-ray diagnosis apparatus 100 is capable of performing the path estimating process and the guiding process explained above, by using a plurality of pieces of projection image data of which projection directions are mutually different.

In the present embodiments, the examples are explained in which the single piece of processing circuitry (the processing circuitry 25) realizes the processing functions explained below; however, another arrangement is also acceptable in which processing circuitry is structured by combining together a plurality of independent processors, so that the functions are realized as a result of the processors executing the programs.

The term "processor" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs saved in the storage 24. In this situation, instead of saving the programs in the storage 24, it is also acceptable to directly incorporate the programs in the circuits of the processors. In that situation, the processors realize the functions thereof by reading and executing the programs incorporated in the circuits thereof. Further, the processors in the present embodiments do not each necessarily have to be structured as a single circuit. It is also acceptable to structure one processor by combining together a plurality of independent circuits so as to realize the functions thereof. Further, it is also acceptable to integrate the plurality of constituent elements in each of the drawings into one processor so as to realize the functions thereof.

Further, the constituent elements of the apparatuses and the devices illustrated in the drawings are based on functional concepts. Thus, it is not necessary to physically configure the constituent elements as indicated in the drawings. In other words, the specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Furthermore, all or an arbitrary part of the processing functions performed by the apparatuses and the devices may be realized by a CPU and a program that is analyzed and executed by the CPU or may be realized as hardware using wired logic.

With regard to the processes explained in the embodiments described above, it is acceptable to manually perform a part of the processes described as being performed automatically. Conversely, by using a method that is publicly known, it is also acceptable to automatically perform all or a part of the processes described as being performed manually. Further, unless noted otherwise, it is acceptable to arbitrarily modify any of the processing procedures, the controlling procedures, specific names, and various information including various types of data and parameters that are presented in the above text and the drawings.

Further, the image processing methods explained in the above embodiments may be realized by causing a computer such as a personal computer or a workstation to execute an image processing computer program prepared in advance. The image processing methods may be distributed via a network such as the Internet. Further, the image processing methods may be recorded on a computer-readable recording medium such as a hard disk, a flexible disk (FD), Compact Disk Read-Only Memory (CD-ROM), a Magneto-Optical (MO) disk, a Digital Versatile Disk (DVD), or the like, so as to be executed as being read from the recording medium by a computer.

In the embodiments and the modification examples described above, the phrase "real-time manner" means that a process is instantly performed every time each piece of data serving as a processing target occurs. For example, a process of displaying an image in a real-time manner is a concept that includes, not only the situation in which the time at which an image of a patient is taken completely coincides with the time at which the image is displayed, but also the situation in which the image is displayed with a slight delay due to the time period required by processes such as an image processing process.

According to at least one aspect of the embodiments described above, it is possible to assist the catheter guiding process.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnosis apparatus comprising processing circuitry configured to:
   extract, from medical image data used for determining a path through which a surgical device is to be inserted, image data containing characteristic information corresponding to a characteristic site in a lumen that may be a constraint during insertion of the surgical device;
   determine, on a basis of the image data corresponding to the characteristic site, an appropriate tip end direction of the surgical device in each of a plurality of positions on the path, the tip end direction being an angle of an axial rotation defined in accordance with a curved shape of a tip end part of the surgical device or a shape of the tip end part after being arranged to curve; and output, as path information, the angle of the axial rotation in each of the positions on the path.

2. The X-ray diagnosis apparatus according to claim 1, wherein the surgical device is one selected from between a guide wire and a catheter of which a tip end part is curved with respect to an axis thereof, and as the tip end direction, the processing circuitry determines an angle of an axial rotation defined in accordance with a curved shape of the tip end part.

3. The X-ray diagnosis apparatus according to claim 1, wherein the surgical device is a catheter of which it is possible to arrange a tip end part to curve with respect to an axis thereof, and as the tip end direction, the processing circuitry determines a direction of the tip end part after being arranged to curve.

4. The X-ray diagnosis apparatus according to claim 1, wherein the tip end direction is a direction intersecting a direction in which a main axis part is extending, the main axis part being continuous to a tip end part of the surgical device.

5. The X-ray diagnosis apparatus according to claim 1, wherein as the path information, the processing circuitry displays a rendering image of the medical image data in which a pixel value corresponding to the tip end direction is assigned to each of the positions on the path, and the processing circuitry displays a direction scale indicating a direction corresponding to each of the pixel values.

6. The X-ray diagnosis apparatus according to claim 5, wherein the processing circuitry further generates an X-ray image, and the processing circuitry displays the X-ray image, together with the rendering image and the direction scale.

7. The X-ray diagnosis apparatus according to claim 6, wherein the processing circuitry further detects, from the X-ray image, a tip end position of the surgical device being inserted in a patient, the processing circuitry performs a position aligning process between the X-ray image and the medical image data, and on a basis of a result of the position aligning process, the processing circuitry displays a marker indicating the tip end position, in a position corresponding to the tip end position within the rendering image.

8. The X-ray diagnosis apparatus according to claim 7, wherein the processing circuitry further detects, in the X-ray image, a current tip end direction of the surgical device being inserted in the patient, and the processing circuitry displays a marker indicating the detected current tip end direction, on the direction scale.

9. The X-ray diagnosis apparatus according to claim 8, wherein, on a basis of a difference between the detected current tip end direction and the tip end direction included in the path information, the processing circuitry displays, on the direction scale, a marker indicating a rotating direction into which the surgical device is to be rotated.

10. The X-ray diagnosis apparatus according to claim 7, wherein the processing circuitry displays, on an inner circumferential side of the direction scale, projection image data in which an interior of the lumen is projected by using the tip end position as a viewpoint.

11. The X-ray diagnosis apparatus according to claim 5, wherein the processing circuitry displays, on the direction scale, a schematic drawing of the characteristic site.

12. The X-ray diagnosis apparatus according to claim 1, wherein the characteristic site is at least one selected from among: a branching part and a curving part of a blood vessel into which the surgical device is to be inserted; a structure formed in the blood vessel; and a part in which a blood vessel wall is thin.

13. The X-ray diagnosis apparatus according to claim 12, wherein, when one selected from between the branching part and the curving part is extracted as the characteristic site, the processing circuitry determines the tip end direction in such a manner that a tip end of the surgical device is directed toward an advancing direction thereof.

14. The X-ray diagnosis apparatus according to claim 12, wherein, when one selected from between the structure and the part in which the blood vessel wall is thin is extracted as the characteristic site, the processing circuitry determines the tip end direction in such a manner that the surgical device will not touch the one selected from between the structure and the part in which the blood vessel wall is thin.

15. The X-ray diagnosis apparatus according to claim 1, wherein the processing circuitry displays rendering images corresponding to a plurality of temporal phases and being respectively generated from pieces of medical image data over a plurality of temporal phases that correspond to at least one heartbeat, while switching between the rendering images in accordance with an electrocardiographic signal of the patient.

16. The X-ray diagnosis apparatus according to claim 1, wherein the medical image data is one selected from between three-dimensional image data and a plurality of pieces of projection image data of which projection directions are mutually different.

17. The X-ray diagnosis apparatus according to claim 1, wherein the processing circuitry configured to extract image data corresponding to the characteristic site comprises processing circuitry configured to perform pattern matching to extract the image data containing characteristic information corresponding to the characteristic site.

18. A medical image processing apparatus comprising a processing circuitry configured to:

extract, from medical image data used for determining a path through which a surgical device is to be inserted, image data containing characteristic information corresponding to a characteristic site in a lumen that may be a constraint during insertion of the surgical device;

determine, on a basis of the image data corresponding to the characteristic site, an appropriate tip end direction defined in accordance with a curved shape of a tip end part of the surgical device, in each of a plurality of positions on the path, the tip end direction being an angle of an axial rotation defined in accordance with a curved shape of a tip end part of the surgical device or a shape of the tip end part after being arranged to curve; and output, as path information, the angle of the axial rotation in each of the positions on the path.

19. A medical image processing system comprising a medical image processing apparatus and an X-ray diagnosis apparatus, wherein the medical image processing apparatus including processing circuitry configured to:

extract, from medical image data used for determining a path through which a surgical device is to be inserted, image data containing characteristic information corresponding to a characteristic site in a lumen that may be a constraint during insertion of the surgical device; and determine, on a basis of the image data corresponding to the characteristic site, an appropriate tip end direction defined in accordance with a curved shape of a tip end part of the surgical device in each of a plurality of positions on the path, the tip end direction being an angle of an axial rotation defined in accordance with a curved shape of a tip end part of the surgical device or a shape of the tip end part after being arranged to curve, and the X-ray diagnosis apparatus including processing circuitry configured to output, as path information, the angle of the axial rotation in each of the positions on the path.

20. A medical image processing method comprising:

extracting, from medical image data used for determining a path through which a surgical device is to be inserted, image data containing characteristic information corresponding to a characteristic site in a lumen that may be a constraint during insertion of the surgical device;

determining, on a basis of the image data corresponding to the characteristic site, an appropriate tip end direction defined in accordance with a curved shape of a tip end part of the surgical device in each of a plurality of positions on the path, the tip end direction being an angle of an axial rotation defined in accordance with a curved shape of a tip end part of the surgical device or a shape of the tip end part after being arranged to curve; and outputting, as path information, the angle of the axial rotation in each of the positions on the path.

* * * * *